(12) United States Patent
Tan et al.

(10) Patent No.: US 6,284,255 B1
(45) Date of Patent: Sep. 4, 2001

(54) COMPOUNDS AND METHODS FOR TREATMENT AND DIAGNOSIS OF MYCOBACTERIAL INFECTIONS

(75) Inventors: Paul Tan; Jun Hiyama; Elizabeth Visser; Linda Scott, all of Auckland (NZ)

(73) Assignee: Genesis Research & Development Corporation Limited, Parnell (NZ)

( * ) Notice: Subject to any disclaimer, the term of this patent is extended or adjusted under 35 U.S.C. 154(b) by 0 days.

(21) Appl. No.: 08/705,347

(22) Filed: Aug. 29, 1996

(51) Int. Cl.[7] .............................. A61K 39/04; C12N 1/00; A01N 37/18; C07H 21/04
(52) U.S. Cl. ............................ 424/248.1; 424/168.1; 424/184.1; 424/185.1; 424/192.1; 435/253.1; 435/863; 514/2; 514/924; 530/350; 536/23.4
(58) Field of Search .............................. 424/248.1, 184.1, 424/185.1, 168.1, 192.1; 530/350; 514/2, 924; 435/253.1, 863; 536/23.4

(56) References Cited

U.S. PATENT DOCUMENTS

| | | |
|---|---|---|
| 3,956,481 | 5/1976 | Jolles et al. . |
| 4,036,953 | 7/1977 | Adam et al. . |
| 4,716,038 | 12/1987 | Stanford et al. . |
| 4,724,144 | * 2/1988 | Rook et al. . |
| 4,879,213 | * 11/1989 | Fox et al. . |
| 5,599,545 | 2/1997 | Stanford et al. . |

FOREIGN PATENT DOCUMENTS

| | | | |
|---|---|---|---|
| 0763361 | 3/1997 | (EP) | .............................. A61K/39/04 |
| 9007935 | 7/1990 | (WO) | .............................. A61K/39/02 |
| 9101751 | 2/1991 | (WO) | .............................. A61K/39/04 |
| 9102542 | 3/1991 | (WO) | .............................. A61K/39/04 |
| 9208488 | * 5/1992 | (WO) | . |
| 9208484 | 5/1992 | (WO) | .............................. A61K/39/04 |
| 9316727 | 9/1993 | (WO) | .............................. A61K/39/04 |
| 9406466 | 3/1994 | (WO) | .............................. A61K/39/04 |
| 9514713 | * 6/1995 | (WO) | . |
| 9526742 | 3/1998 | (WO) | .............................. A61K/39/04 |
| 9526742 | 3/2001 | (WO) | .............................. A61K/39/04 |

OTHER PUBLICATIONS

Smith, Elements of Molecular Neurobiology, 2nd edition, p.48–50, 1996.*
Khandekar et al. Int. J. Lepr. Other Mycobact Dis. Sep. 1986, 54(3), 416–22.*
Lazar et al. Mol. & Cell. Biol. 1988 8 (3), 1247–1252.*
Burgess et al. J. Cell. Biol. 1990, 111, 2129–2138.*
R.G. White et al., "Correlation of Adjuvant Activity and Chemical Structure of Wax D Fractions of Mycobacteria," Immunology 7, pp. 158–171, 1964.
R.G. White, "Characterization of Micobacterial Components of Adjuvant Mixtures," Symposium Series Immunobiol. Standard 6, pp. 49–58, 1967.
R.G. White et al., The Influence of Components of M. Tuberculosis and other Mycobacteria upon Antibody Production to Ovalbumin, Immunology I, pp. 54–66, 1958.
Philip Peake et al., Mechanism of Interaction of the 85B Secreted Protein of *Mycobacterium bovis* with Fibronectin, *Infection and Immunity*, pp. 4828–4834, Nov. 1993.

* cited by examiner

Primary Examiner—Rodney P. Swartz
(74) Attorney, Agent, or Firm—Ann W. Speckman; Janet Sleath

(57) ABSTRACT

The present invention provides polypeptides comprising an immunogenic portion of a *M. vaccae* soluble protein and DNA molecules encoding such polypeptides, together with methods for their use in the diagnosis and treatment of mycobacterial infection. Methods for enhancing the immune response to an antigen including administration of *M. vaccae* culture filtrate or delipidated *M. vaccae* cells are also provided.

19 Claims, 9 Drawing Sheets

```
M. vaccae:   MRLLDRIRGPW...ARRFGVV.AVATAMMPALVGLAGGSATAGAFSRPGLPVEYLMVPSP
m. bovis:    MQLVDRVRGAVTGMSRRL.VVGAVGAALVSGLVGAVGGTATAGAFSRPGLPVEYLQVPSP
M. tb:       MQLVDRVRGAVTGMSRRL.VVGAVAR.LVSGLVGAVGGTATAGAFSRPGLPVEYLQVPSP
m. leprae.   MKFVDRFRGAVAGMLRRL.VVEAMGVALLSALIGVVG.SAPAEAFSRPGLPVEYLQVPSP
CONSENSUS:   M   DR RG        RR VV A           L  G   G   A  A AFSRPGLPVEYL VPSP M. vaccae:   SMGRDIKIQFQSGGENSPALYLLDGLRAQEDFNGWDINTQAFEWFLDSGISVVMPVGGQS
m. bovis:    SMGRDIKVQFQSGGANSPALYLLDGLRAQDDFSGWDINTPAFEWYDQSGLSVVMPVGGQS
M. tb:       SMGRDIKVQFQSGGANSPALYLLDGLRAQDDFSGWDINTPAFEWYDQSGLSVVMPVGGQS
M. leprae:   SMGRDIKVQFQNGGANSPALYLLDGLRAQDDFSGWDINTTAFEWYYQSGISVVMPVGGQS
CONSENSUS:   SMGRDIK QFQ GG NSPALYLLDGLRA   F GWDINT AFEW   SG SVVMPVGGQS M. vaccae:   SFYTDWYAPARNKGPTVTYKWETFLTQELPGWLQANRAVKPTGSGPVGLSMAGSAALNLA
M. bovis:    SFYSDWYQPACGKAGCQTYKWETFLTSELPGWLQANRHVKPTGSAVVGLSMAASSALTLA
M. tb:       SFYSDWYQPACRKAGCQTYKWETFLTSELPGWLQANRHVKPTGSAVVGLSMAASSALTLA
M. leprae:   SFYSDWYSPACGKAGCQTYKWETFLTSELPEYLQSNKQIKPTGSAAVGLSMAGLSALTLA
CONSENSUS:   SFY DWY PA  K    TYKWETFLT ELP  LQ N   KPTGS  VGLSMA   AL LA M. vaccae:   TWHPEQFIYAGSMSGFLNPSEGWWPFLINISMGDAGGFKADDMWGKTEGIPTAVGQRNDP
M. bovis:    IYHPQQFVYAGAMSGLLDPSQAMGPTLIGLAMGDAGGYKASDMWGPKEDPAW...QRNDP
M. tb:       IYHPQQFVYAGAMSGLLDPSQAMGPTLIGLAMGDAGGYKASDMWGPKEDPAW...QRNDP
M. leprae:   IYHPDQFIYVGSMSGLLDPSNAMGPSLIGLAMGDAGGYKAADMWGPSTDPAW...KRNDP
CONSENSUS:      HP QF Y G MSG L PS    P LI  MGDAGG KA DMWG         RNDP M. vaccae:   MLNIPTLVANNTRIWVYCGNGQPTELGGGDLPATFLEGLTIRT.NETFRDNYIAAGGHNG
m. bovis:    LLNVGKLIANNTRVWVYCGNGKPSDLGGNNLPAKFLEGF.VRTSNIKFQDAYNAGGGHNG
M. tb:       LLNVGKLIANNTRVWVYCGNGKPSDLGGNNLPAKFLEGF.VRTSNIKFQDAYNAGGRHNG
M. leprae:   TVNVGTLIANNTRIWMYCGNGKPTELGGNNLPAKLLEGL.VRTSNIKFQDGYNAGGGHNA
CONSENSUS:      N   L ANNTR W YCGNG P  LGG  LPA  LEG    RT N   F D Y AGG HN M. vaccae:   VFNFPANGTHNWAYWGRELQAMKPDLQAHLL*
M. bovis:    VFDFPDSGTHSWEYWGAQLNAMKPDLQRALGATPNTGPAPQGA*
M. tb:       VFDFPDSGTHSWEYWGAQLNAMKPDLQRHWVPRPTPGP.PQGA*
M. leprae:   VFNFPDSGTHSWEYWGEQLNDMKPDLQQYLGAT..PGA*
CONSENSUS:   VF FP  GTH W YWG  L  MKPDLQ
```

*Fig. 3*

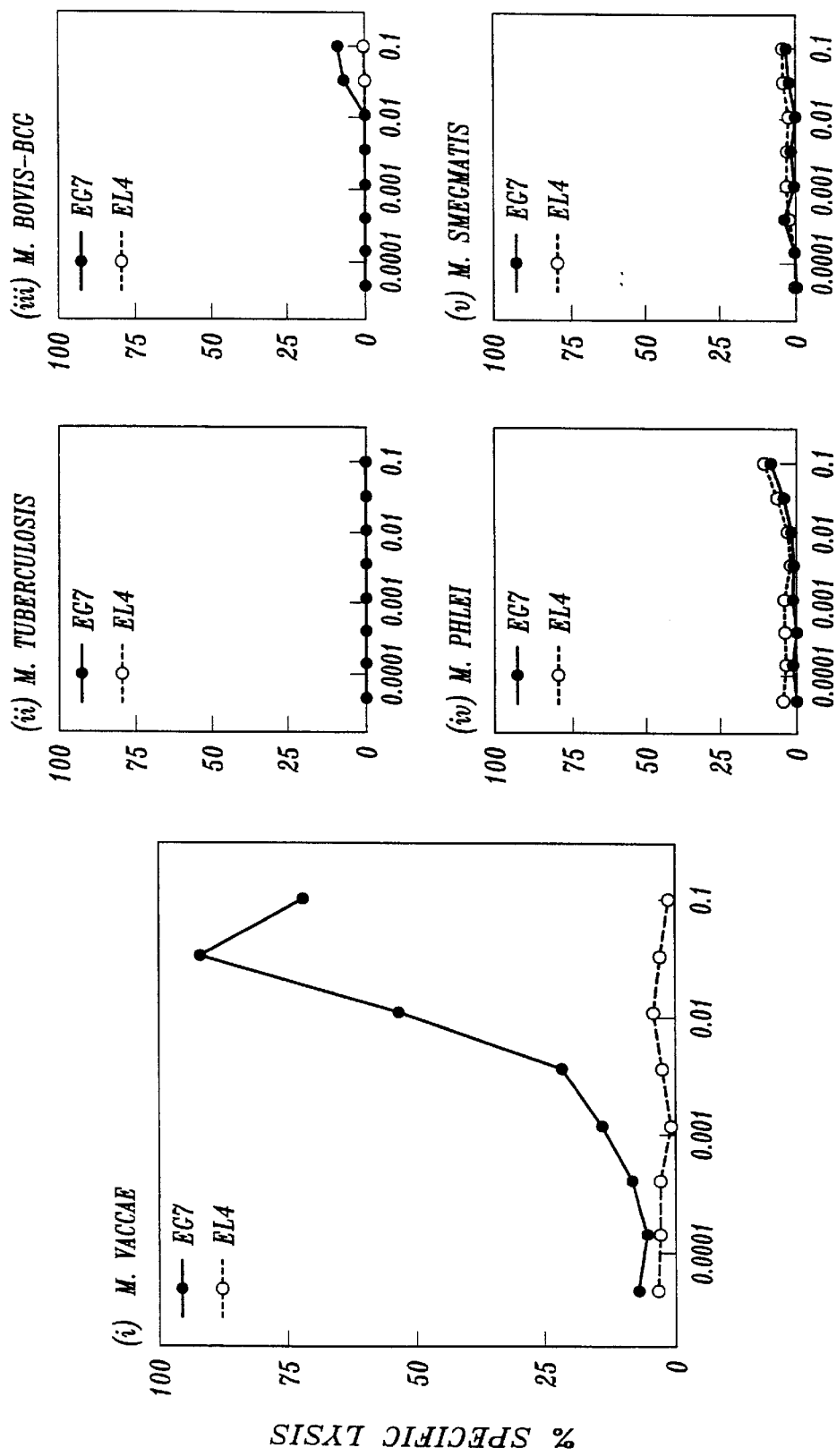

SEQUENCE LISTING (1) GENERAL INFORMATION:

(iii) NUMBER OF SEQUENCES: 55

(2) INFORMATION FOR SEQ ID NO:1:

(i) SEQUENCE CHARACTERISTICS:
      (A) LENGTH: 25 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

Ala Pro Val Gly Pro Gly Xaa Ala Ala Tyr Val Gln Gln Val Pro Asp
1               5                   10                  15

Gly Pro Gly Ser Val Gln Gly Met Ala
            20                  25

(2) INFORMATION FOR SEQ ID NO:2:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Met Xaa Asp Gln Leu Lys Val Asn Asp Asp
1               5                   10

(2) INFORMATION FOR SEQ ID NO:3:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Met Xaa Pro Val Pro Val Ala Thr Ala Ala Tyr
1               5                   10

(2) INFORMATION FOR SEQ ID NO:4:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Thr Pro Ala Pro Ala Pro Pro Tyr Val Asp His Val Glu Gln Ala
1               5                   10                  15

Lys Phe Gly Asp Leu
            20

(2) INFORMATION FOR SEQ ID NO:5:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Met Gln Ala Phe Asn Ala Asp Ala Tyr Ala Phe Ala Lys Arg Glu Lys
1               5                   10                  15

Val Ser Leu Ala Pro Gly Val Pro Xaa Val Phe Glu Thr
            20                  25

(2) INFORMATION FOR SEQ ID NO:6:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Met Ala Asp Pro Asn Xaa Ala Ile Leu Gln Val Ser Lys Thr Thr Arg
1               5                  10                  15

Gly Gly Gln Ala Ala
            20
```

(2) INFORMATION FOR SEQ ID NO:7:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Met Pro Ile Leu Gln Val Ser Gln Thr Gly Arg
1               5                  10
```

(2) INFORMATION FOR SEQ ID NO:8:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Met Xaa Asp Pro Ile Xaa Leu Gln Leu Gln Val Ser Ser Thr
1               5                  10
```

(2) INFORMATION FOR SEQ ID NO:9:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
Lys Ala Thr Tyr Val Gln Gly Gly Leu Gly Arg Ile Glu Ala Arg Val
1               5                  10                  15
```

(2) INFORMATION FOR SEQ ID NO:10:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

```
Lys Xaa Gly Leu Ala Asp Leu Ala Pro
1               5
```

(2) INFORMATION FOR SEQ ID NO:11:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Modified-site
        (B) LOCATION: 12
        (D) OTHER INFORMATION: /note= "Residue can be either Glu
            or Ile"

(xi) SEQUENCE DESCRIPTION: SEQ ID NO:11:

```
Lys Xaa Tyr Ala Leu Ala Leu Met Ser Ala Val Xaa Ala Ala
1               5                   10
```

(2) INFORMATION FOR SEQ ID NO:12:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

```
Lys Asn Pro Gln Val Ser Asp Glu Leu Xaa Thr
1               5                   10
```

(2) INFORMATION FOR SEQ ID NO:13:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

```
Ala Pro Ala Pro Ala Ala Pro Ala Xaa Gly Asp Pro Ala Ala Val Val
1               5                   10                  15

Ala Ala Asn Ser Thr
            20
```

(2) INFORMATION FOR SEQ ID NO:14:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

```
Glu Ala Glu Val Xaa Tyr Leu Gly Gln Pro Gly Glu Leu Val Asn
1               5                   10                  15
```

(2) INFORMATION FOR SEQ ID NO:15:

```
    (i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Modified-site
        (B) LOCATION: 2
        (D) OTHER INFORMATION: /note= "Residue can be either Gly
            or Ala"

(ix) FEATURE:
        (A) NAME/KEY: Modified-site
        (B) LOCATION: 15
        (D) OTHER INFORMATION: /note= "Residue can be either Pro
            or Ala"

(xi) SEQUENCE DESCRIPTION: SEQ ID NO:15:

Ala Xaa Val Val Pro Pro Xaa Gly Pro Pro Ala Pro Gly Ala Xaa
1               5                  10                  15

(2) INFORMATION FOR SEQ ID NO:16:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

Ala Pro Ala Pro Asp Leu Gln Gly Pro Leu Val Ser Thr Leu Ser
1               5                  10                  15

(2) INFORMATION FOR SEQ ID NO:17:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

Ala Thr Pro Asp Trp Ser Gly Arg Tyr Thr Val Val Thr Phe Ala Ser
1               5                  10                  15

Asp Lys Leu Gly Thr Ser Val Ala Ala
            20                  25

(2) INFORMATION FOR SEQ ID NO:18:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Modified-site
        (B) LOCATION: 15
        (D) OTHER INFORMATION: /note= "Residue can be either Ala
            or Arg"

(ix) FEATURE:
```

(A) NAME/KEY: Modified-site
            (B) LOCATION: 23
            (D) OTHER INFORMATION: /note= "Residue can be either Val
                or Leu"

(xi) SEQUENCE DESCRIPTION: SEQ ID NO:18:

Ala Pro Pro Tyr Asp Asp Arg Gly Tyr Val Asp Ser Thr Ala Xaa Xaa
1               5                   10                  15

Ala Ser Pro Pro Thr Leu Xaa Val Val
            20                  25

(2) INFORMATION FOR SEQ ID NO:19:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:19:

Glu Pro Glu Gly Val Ala Pro Pro
1               5

(2) INFORMATION FOR SEQ ID NO:20:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:20:

Glu Pro Ala Gly Ile Pro Ala Gly Phe Pro Asp Val Ser Ala Tyr Ala
1               5                   10                  15

Ala Val Asp Pro Xaa Xaa Tyr Val Val
            20                  25

(2) INFORMATION FOR SEQ ID NO:21:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:21:

Ala Pro Val Gly Pro Gly Xaa Ala Ala Tyr Val Gln Gln Val Pro
1               5                   10                  15

(2) INFORMATION FOR SEQ ID NO:22:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:22:

Phe Ser Arg Pro Gly Leu Pro Val Glu Tyr Leu Asp Val Phe Ser
1               5                   10                  15

(2) INFORMATION FOR SEQ ID NO:23:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:23:

```
Phe Ser Arg Pro Gly Leu Pro Val Glu Tyr Leu Asn Val Pro Ser Pro
1               5                   10                  15
Ser Met Gly
```

(2) INFORMATION FOR SEQ ID NO:24:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:24:

```
Phe Ser Arg Pro Gly Leu Pro Val Glu Tyr Leu Asn Val Pro Val Ser
1               5                   10                  15
```

(2) INFORMATION FOR SEQ ID NO:25:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:25:

```
Xaa Xaa Thr Gly Leu His Arg Leu Arg Met Met Val Pro Asn
1               5                   10
```

(2) INFORMATION FOR SEQ ID NO:26:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Modified-site
        (B) LOCATION: 16
        (D) OTHER INFORMATION: /note= "Residue can be either Ser
           or Val"

(ix) FEATURE:
        (A) NAME/KEY: Modified-site
        (B) LOCATION: 17
        (D) OTHER INFORMATION: /note= "Residue can be either Gln
           or Val"

(xi) SEQUENCE DESCRIPTION: SEQ ID NO:26:

```
Val Pro Ala Asp Pro Val Gly Ala Ala Ala Gln Ala Glu Pro Ala Xaa
1               5                   10                  15
```

```
Xaa Arg Ile Asp
          20
```

(2) INFORMATION FOR SEQ ID NO:27:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Modified-site
        (B) LOCATION: 4
        (D) OTHER INFORMATION: /note= "Residue can be either Tyr
            or Pro"

(ix) FEATURE:
        (A) NAME/KEY: Modified-site
        (B) LOCATION: 8
        (D) OTHER INFORMATION: /note= "Residue can be either Val
            or Gly"

(ix) FEATURE:
        (A) NAME/KEY: Modified-site
        (B) LOCATION: 9
        (D) OTHER INFORMATION: /note= "Residue can be either Ile
            or Tyr"

(xi) SEQUENCE DESCRIPTION: SEQ ID NO:27:

```
Asp Pro Xaa Xaa Asp Ile Glu Xaa Xaa Phe Ala Arg Gly Thr
1               5                   10
```

(2) INFORMATION FOR SEQ ID NO:28:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:28:

```
Ala Pro Ser Leu Ser Val Ser Asp Tyr Ala Arg Asp Ala Gly Phe
1               5                   10                  15
```

(2) INFORMATION FOR SEQ ID NO:29:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Modified-site
        (B) LOCATION: 2
        (D) OTHER INFORMATION: /note= "Residue can be either Leu
            or Pro"

(xi) SEQUENCE DESCRIPTION: SEQ ID NO:29:

```
Xaa Xaa Leu Ala Xaa Ala Xaa Leu Gly Xaa Thr Val Asp Ala Asp Gln
1               5                   10                  15
```

(2) INFORMATION FOR SEQ ID NO:30:

(i) SEQUENCE CHARACTERISTICS:

(A) LENGTH: 330 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:30:

Met Lys Phe Val Asp Arg Phe Arg Gly Ala Val Ala Gly Met Leu Arg
1               5                   10                  15

Arg Leu Val Val Glu Ala Met Gly Val Ala Leu Leu Ser Ala Leu Ile
                20                  25                  30

Gly Val Val Gly Ser Ala Pro Ala Glu Ala Phe Ser Arg Pro Gly Leu
            35                  40                  45

Pro Val Glu Tyr Leu Gln Val Pro Ser Pro Ser Met Gly Arg Asp Ile
        50                  55                  60

Lys Val Gln Phe Gln Asn Gly Gly Ala Asn Ser Pro Ala Leu Tyr Leu
65                  70                  75                  80

Leu Asp Gly Leu Arg Ala Gln Asp Asp Phe Ser Gly Trp Asp Ile Asn
                85                  90                  95

Thr Thr Ala Phe Glu Trp Tyr Tyr Gln Ser Gly Ile Ser Val Val Met
                100                 105                 110

Pro Val Gly Gly Gln Ser Ser Phe Tyr Ser Asp Trp Tyr Ser Pro Ala
            115                 120                 125

Cys Gly Lys Ala Gly Cys Gln Thr Tyr Lys Trp Glu Thr Phe Leu Thr
130                 135                 140

Ser Glu Leu Pro Glu Tyr Leu Gln Ser Asn Lys Gln Ile Lys Pro Thr
145                 150                 155                 160

Gly Ser Ala Ala Val Gly Leu Ser Met Ala Gly Leu Ser Ala Leu Thr
                165                 170                 175

Leu Ala Ile Tyr His Pro Asp Gln Phe Ile Tyr Val Gly Ser Met Ser
                180                 185                 190

Gly Leu Leu Asp Pro Ser Asn Ala Met Gly Pro Ser Leu Ile Gly Leu
            195                 200                 205

Ala Met Gly Asp Ala Gly Gly Tyr Lys Ala Ala Asp Met Trp Gly Pro
        210                 215                 220

Ser Thr Asp Pro Ala Trp Lys Arg Asn Asp Pro Thr Val Asn Val Gly
225                 230                 235                 240

Thr Leu Ile Ala Asn Asn Thr Arg Ile Trp Met Tyr Cys Gly Asn Gly
                245                 250                 255

Lys Pro Thr Glu Leu Gly Gly Asn Asn Leu Pro Ala Lys Leu Leu Glu
            260                 265                 270

Gly Leu Val Arg Thr Ser Asn Ile Lys Phe Gln Asp Gly Tyr Asn Ala
        275                 280                 285

Gly Gly Gly His Asn Ala Val Phe Asn Phe Pro Asp Ser Gly Thr His
        290                 295                 300

Ser Trp Glu Tyr Trp Gly Glu Gln Leu Asn Asp Met Lys Pro Asp Leu
305                 310                 315                 320

Gln Gln Tyr Leu Gly Ala Thr Pro Gly Ala
                325                 330

(2) INFORMATION FOR SEQ ID NO:31:

(i) SEQUENCE CHARACTERISTICS:
        (A) LENGTH: 327 amino acids
        (B) TYPE: amino acid
        (C) STRANDEDNESS: single (D) TOPOLOGY: linear (ii) MOLECULE TYPE: protein (xi) SEQUENCE DESCRIPTION: SEQ ID NO:31:

Met Ile Asp Val Ser Gly Lys Ile Arg Ala Trp Gly Arg Trp Leu Leu
1               5                   10                  15

Val Gly Ala Ala Ala Thr Leu Pro Ser Leu Ile Ser Leu Ala Gly Gly
            20                  25                  30

Ala Ala Thr Ala Ser Ala Phe Ser Arg Pro Gly Leu Pro Val Glu Tyr
            35                  40                  45

Leu Gln Val Pro Ser Glu Ala Met Gly Arg Thr Ile Lys Val Gln Phe
        50                  55                  60

Gln Asn Gly Gly Asn Gly Ser Pro Ala Val Tyr Leu Leu Asp Gly Leu
65                  70                  75                  80

Arg Ala Gln Asp Asp Tyr Asn Gly Trp Asp Ile Asn Thr Ser Ala Phe
                85                  90                  95

Glu Trp Tyr Tyr Gln Ser Gly Leu Ser Val Val Met Pro Val Gly Gly
            100                 105                 110

Gln Ser Ser Phe Tyr Ser Asp Trp Tyr Ser Pro Ala Cys Gly Lys Ala
            115                 120                 125

Gly Cys Thr Thr Tyr Lys Trp Glu Thr Phe Leu Thr Ser Glu Leu Pro
            130                 135                 140

Lys Trp Leu Ser Ala Asn Arg Ser Val Lys Ser Thr Gly Ser Ala Val
145                 150                 155                 160

Val Gly Leu Ser Met Ala Gly Ser Ser Ala Leu Ile Leu Ala Ala Tyr
                165                 170                 175

His Pro Asp Gln Phe Ile Tyr Ala Gly Ser Leu Ser Ala Leu Met Asp
            180                 185                 190

Ser Ser Gln Gly Ile Glu Pro Gln Leu Ile Gly Leu Ala Met Gly Asp
            195                 200                 205

Ala Gly Gly Tyr Lys Ala Ala Asp Met Trp Gly Pro Pro Asn Asp Pro
        210                 215                 220

Ala Trp Gln Arg Asn Asp Pro Ile Leu Gln Ala Gly Lys Leu Val Ala
225                 230                 235                 240

Asn Asn Thr His Leu Trp Val Tyr Cys Gly Asn Gly Thr Pro Ser Glu
                245                 250                 255

Leu Gly Gly Thr Asn Val Pro Ala Glu Phe Leu Glu Asn Phe Val His
            260                 265                 270

Gly Ser Asn Leu Lys Phe Gln Asp Ala Tyr Asn Gly Ala Gly Gly His
            275                 280                 285

Asn Ala Val Phe Asn Leu Asn Ala Asp Gly Thr His Ser Trp Glu Tyr
            290                 295                 300

Trp Gly Ala Gln Leu Asn Ala Met Lys Pro Asp Leu Gln Asn Thr Leu
305                 310                 315                 320

Met Ala Val Pro Arg Ser Gly
                325

(2) INFORMATION FOR SEQ ID NO:32:

(i) SEQUENCE CHARACTERISTICS:
        (A) LENGTH: 338 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:32:

```
Met Gln Leu Val Asp Arg Val Arg Gly Ala Val Thr Gly Met Ser Arg
1               5                   10                  15
Arg Leu Val Val Gly Ala Val Gly Ala Ala Leu Val Ser Gly Leu Val
                20                  25                  30
Gly Ala Val Gly Gly Thr Ala Thr Ala Gly Ala Phe Ser Arg Pro Gly
            35                  40                  45
Leu Pro Val Glu Tyr Leu Gln Val Pro Ser Pro Ser Met Gly Arg Asp
        50                  55                  60
Ile Lys Val Gln Phe Gln Ser Gly Gly Ala Asn Ser Pro Ala Leu Tyr
65                  70                  75                  80
Leu Leu Asp Gly Leu Arg Ala Gln Asp Asp Phe Ser Gly Trp Asp Ile
                85                  90                  95
Asn Thr Pro Ala Phe Glu Trp Tyr Asp Gln Ser Gly Leu Ser Val Val
                100                 105                 110
Met Pro Val Gly Gly Gln Ser Ser Phe Tyr Ser Asp Trp Tyr Gln Pro
            115                 120                 125
Ala Cys Gly Lys Ala Gly Cys Gln Thr Tyr Lys Trp Glu Thr Phe Leu
        130                 135                 140
Thr Ser Glu Leu Pro Gly Trp Leu Gln Ala Asn Arg His Val Lys Pro
145                 150                 155                 160
Thr Gly Ser Ala Val Val Gly Leu Ser Met Ala Ala Ser Ser Ala Leu
                165                 170                 175
Thr Leu Ala Ile Tyr His Pro Gln Gln Phe Val Tyr Ala Gly Ala Met
                180                 185                 190
Ser Gly Leu Leu Asp Pro Ser Gln Ala Met Gly Pro Thr Leu Ile Gly
            195                 200                 205
Leu Ala Met Gly Asp Ala Gly Gly Tyr Lys Ala Ser Asp Met Trp Gly
        210                 215                 220
Pro Lys Glu Asp Pro Ala Trp Gln Arg Asn Asp Pro Leu Leu Asn Val
225                 230                 235                 240
Gly Lys Leu Ile Ala Asn Asn Thr Arg Val Trp Val Tyr Cys Gly Asn
                245                 250                 255
Gly Lys Pro Ser Asp Leu Gly Gly Asn Asn Leu Pro Ala Lys Phe Leu
                260                 265                 270
Glu Gly Phe Val Arg Thr Ser Asn Ile Lys Phe Gln Asp Ala Tyr Asn
            275                 280                 285
Ala Gly Gly His Asn Gly Val Phe Asp Phe Pro Asp Ser Gly Thr
        290                 295                 300
His Ser Trp Glu Tyr Trp Gly Ala Gln Leu Asn Ala Met Lys Pro Asp
305                 310                 315                 320
Leu Gln Arg Ala Leu Gly Ala Thr Pro Asn Thr Gly Pro Ala Pro Gln
                325                 330                 335
Gly Ala
```

(2) INFORMATION FOR SEQ ID NO:33:

(i) SEQUENCE CHARACTERISTICS:
        (A) LENGTH: 325 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:33:

```
Met Thr Asp Val Ser Arg Lys Ile Arg Ala Trp Gly Arg Arg Leu Met
1               5                   10                  15

Ile Gly Thr Ala Ala Ala Val Val Leu Pro Gly Leu Val Gly Leu Ala
            20                  25                  30

Gly Gly Ala Ala Thr Ala Gly Ala Phe Ser Arg Pro Gly Leu Pro Val
            35                  40                  45

Glu Tyr Leu Gln Val Pro Ser Pro Ser Met Gly Arg Asp Ile Lys Val
        50                  55                  60

Gln Phe Gln Ser Gly Gly Asn Asn Ser Pro Ala Val Tyr Leu Leu Asp
65                  70                  75                  80

Gly Leu Arg Ala Gln Asp Asp Tyr Asn Gly Trp Asp Ile Asn Thr Pro
                85                  90                  95

Ala Phe Glu Trp Tyr Tyr Gln Ser Gly Leu Ser Ile Val Met Pro Val
            100                 105                 110

Gly Gly Gln Ser Ser Phe Tyr Ser Asp Trp Tyr Ser Pro Ala Cys Gly
            115                 120                 125

Lys Ala Gly Cys Gln Thr Tyr Lys Trp Glu Thr Phe Leu Thr Ser Glu
130                 135                 140

Leu Pro Gln Trp Leu Ser Ala Asn Arg Ala Val Lys Pro Thr Gly Ser
145                 150                 155                 160

Ala Ala Ile Gly Leu Ser Met Ala Gly Ser Ser Ala Met Ile Leu Ala
                165                 170                 175

Ala Tyr His Pro Gln Gln Phe Ile Tyr Ala Gly Ser Leu Ser Ala Leu
            180                 185                 190

Leu Asp Pro Ser Gln Gly Met Gly Pro Ser Leu Ile Gly Leu Ala Met
            195                 200                 205

Gly Asp Ala Gly Gly Tyr Lys Ala Ala Asp Met Trp Gly Pro Ser Ser
210                 215                 220

Asp Pro Ala Trp Glu Arg Asn Asp Pro Thr Gln Gln Ile Pro Lys Leu
225                 230                 235                 240

Val Ala Asn Asn Thr Arg Leu Trp Val Tyr Cys Gly Asn Gly Thr Pro
                245                 250                 255

Asn Glu Leu Gly Gly Ala Asn Ile Pro Ala Glu Phe Leu Glu Asn Phe
            260                 265                 270

Val Arg Ser Ser Asn Leu Lys Phe Gln Asp Ala Tyr Asn Ala Ala Gly
            275                 280                 285

Gly His Asn Ala Val Phe Asn Phe Pro Pro Asn Gly Thr His Ser Trp
290                 295                 300

Glu Tyr Trp Gly Ala Gln Leu Asn Ala Met Lys Gly Asp Leu Gln Ser
305                 310                 315                 320

Ser Leu Gly Ala Gly
            325
```

(2) INFORMATION FOR SEQ ID NO:34:

(i) SEQUENCE CHARACTERISTICS:
        (A) LENGTH: 338 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:34:

Met Gln Leu Val Asp Arg Val Arg Gly Ala Val Thr Gly Met Ser Arg

```
  1               5                   10                  15
Arg Leu Val Val Gly Ala Val Gly Ala Ala Leu Val Ser Gly Leu Val
                    20                  25                  30
Gly Ala Val Gly Gly Thr Ala Thr Ala Gly Ala Phe Ser Arg Pro Gly
                35                  40                  45
Leu Pro Val Glu Tyr Leu Gln Val Pro Ser Pro Ser Met Gly Arg Asp
 50                  55                  60
Ile Lys Val Gln Phe Gln Ser Gly Ala Asn Ser Pro Ala Leu Tyr
 65                  70                  75                  80
Leu Leu Asp Gly Leu Arg Ala Gln Asp Asp Phe Ser Gly Trp Asp Ile
                    85                  90                  95
Asn Thr Pro Ala Phe Glu Trp Tyr Asp Gln Ser Gly Leu Ser Val Val
                100                 105                 110
Met Pro Val Gly Gly Gln Ser Ser Phe Tyr Ser Asp Trp Tyr Gln Pro
                115                 120                 125
Ala Cys Gly Lys Ala Gly Cys Gln Thr Tyr Lys Trp Glu Thr Phe Leu
                130                 135                 140
Thr Ser Glu Leu Pro Gly Trp Leu Gln Ala Asn Arg His Val Lys Pro
145                 150                 155                 160
Thr Gly Ser Ala Val Val Gly Leu Ser Met Ala Ala Ser Ser Ala Leu
                165                 170                 175
Thr Leu Ala Ile Tyr His Pro Gln Gln Phe Val Tyr Ala Gly Ala Met
                180                 185                 190
Ser Gly Leu Leu Asp Pro Ser Gln Ala Met Gly Pro Thr Leu Ile Gly
                195                 200                 205
Leu Ala Met Gly Asp Ala Gly Gly Tyr Lys Ala Ser Asp Met Trp Gly
210                 215                 220
Pro Lys Glu Asp Pro Ala Trp Gln Arg Asn Asp Pro Leu Leu Asn Val
225                 230                 235                 240
Gly Lys Leu Ile Ala Asn Asn Thr Arg Val Trp Val Tyr Cys Gly Asn
                245                 250                 255
Gly Lys Pro Ser Asp Leu Gly Gly Asn Asn Leu Pro Ala Lys Phe Leu
                260                 265                 270
Glu Gly Phe Val Arg Thr Ser Asn Ile Lys Phe Gln Asp Ala Tyr Asn
                275                 280                 285
Ala Gly Gly His Asn Gly Val Phe Asp Phe Pro Asp Ser Gly Thr
 290                 295                 300
His Ser Trp Glu Tyr Trp Gly Ala Gln Leu Asn Ala Met Lys Pro Asp
305                 310                 315                 320
Leu Gln Arg Ala Leu Gly Ala Thr Pro Asn Thr Gly Pro Ala Pro Gln
                325                 330                 335
Gly Ala
```

(2) INFORMATION FOR SEQ ID NO:35:

(i) SEQUENCE CHARACTERISTICS:
        (A) LENGTH: 323 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:35:

```
Met Thr Asp Val Ser Arg Lys Ile Arg Ala Trp Gly Arg Arg Leu Met
 1               5                  10                  15
```

```
Ile Gly Thr Ala Ala Ala Val Val Leu Pro Gly Leu Val Gly Leu Ala
            20                  25                  30

Gly Gly Ala Ala Thr Ala Gly Ala Phe Ser Arg Pro Gly Leu Pro Val
        35                  40                  45

Glu Tyr Leu Gln Val Pro Ser Pro Ser Met Gly Arg Asp Ile Lys Val
    50                  55                  60

Gln Phe Gln Ser Gly Gly Asn Asn Ser Pro Ala Val Tyr Leu Leu Asp
65                  70                  75                  80

Gly Leu Arg Ala Gln Asp Asp Tyr Asn Gly Trp Asp Ile Asn Thr Pro
                85                  90                  95

Ala Phe Glu Trp Tyr Tyr Gln Ser Gly Leu Ser Ile Val Met Pro Val
            100                 105                 110

Gly Gly Gln Ser Ser Phe Tyr Ser Asp Trp Tyr Ser Pro Ala Cys Gly
        115                 120                 125

Lys Ala Gly Cys Gln Thr Tyr Lys Trp Glu Thr Leu Leu Thr Ser Glu
    130                 135                 140

Leu Pro Gln Trp Leu Ser Ala Asn Arg Ala Val Lys Pro Thr Gly Ser
145                 150                 155                 160

Ala Ala Ile Gly Leu Ser Met Ala Gly Ser Ala Met Ile Leu Ala
                165                 170                 175

Ala Tyr His Pro Gln Gln Phe Ile Tyr Ala Gly Ser Leu Ser Ala Leu
            180                 185                 190

Leu Asp Pro Ser Gln Gly Met Gly Leu Ile Gly Leu Ala Met Gly Asp
        195                 200                 205

Ala Gly Gly Tyr Lys Ala Ala Asp Met Trp Gly Pro Ser Ser Asp Pro
    210                 215                 220

Ala Trp Glu Arg Asn Asp Pro Thr Gln Gln Ile Pro Lys Leu Val Ala
225                 230                 235                 240

Asn Asn Thr Arg Leu Trp Val Tyr Cys Gly Asn Gly Thr Pro Asn Glu
                245                 250                 255

Leu Gly Gly Ala Asn Ile Pro Ala Glu Phe Leu Glu Asn Phe Val Arg
            260                 265                 270

Ser Ser Asn Leu Lys Phe Gln Asp Ala Tyr Lys Pro Ala Gly Gly His
        275                 280                 285

Asn Ala Val Phe Asn Phe Pro Pro Asn Gly Thr His Ser Trp Glu Tyr
    290                 295                 300

Trp Gly Ala Gln Leu Asn Ala Met Lys Gly Asp Leu Gln Ser Ser Leu
305                 310                 315                 320

Gly Ala Gly (2) INFORMATION FOR SEQ ID NO:36:

(i) SEQUENCE CHARACTERISTICS:
        (A) LENGTH: 333 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:36:

Met Lys Phe Leu Gln Gln Met Arg Lys Leu Phe Gly Leu Ala Ala Lys
1               5                   10                  15

Phe Pro Ala Arg Leu Thr Ile Ala Val Ile Gly Thr Ala Leu Leu Ala
            20                  25                  30
```

-continued

```
Gly Leu Val Gly Val Val Gly Asp Thr Ala Ile Ala Val Ala Phe Ser
            35                  40                  45

Lys Pro Gly Leu Pro Val Glu Tyr Leu Gln Val Pro Ser Pro Ser Met
 50                  55                  60

Gly His Asp Ile Lys Ile Gln Phe Gln Gly Gly Gln His Ala Val
 65                  70                  75                  80

Tyr Leu Leu Asp Gly Leu Arg Ala Gln Glu Asp Tyr Asn Gly Trp Asp
                    85                  90                  95

Ile Asn Thr Pro Ala Phe Glu Glu Tyr Tyr His Ser Gly Leu Ser Val
                    100                 105                 110

Ile Met Pro Val Gly Gly Gln Ser Ser Phe Tyr Ser Asn Trp Tyr Gln
            115                 120                 125

Pro Ser Gln Gly Asn Gly Gln His Tyr Thr Tyr Lys Trp Glu Thr Phe
            130                 135                 140

Leu Thr Gln Glu Met Pro Ser Trp Leu Gln Ala Asn Lys Asn Val Leu
145                 150                 155                 160

Pro Thr Gly Asn Ala Ala Val Gly Leu Ser Met Ser Gly Ser Ser Ala
                    165                 170                 175

Leu Ile Leu Ala Ser Tyr Tyr Pro Gln Gln Phe Pro Tyr Ala Ala Ser
                    180                 185                 190

Leu Ser Gly Phe Leu Asn Pro Ser Glu Gly Trp Trp Pro Thr Met Ile
            195                 200                 205

Gly Leu Ala Met Asn Asp Ser Gly Gly Tyr Asn Ala Asn Ser Met Trp
210                 215                 220

Gly Pro Ser Thr Asp Pro Ala Trp Lys Arg Asn Asp Pro Met Val Gln
225                 230                 235                 240

Ile Pro Arg Leu Val Ala Asn Asn Thr Arg Ile Trp Val Tyr Cys Gly
                    245                 250                 255

Asn Gly Ala Pro Asn Glu Leu Gly Gly Asp Asn Ile Pro Ala Lys Phe
                    260                 265                 270

Leu Glu Ser Leu Thr Leu Ser Thr Asn Glu Ile Phe Gln Asn Thr Tyr
            275                 280                 285

Ala Ala Ser Gly Gly Arg Asn Gly Val Phe Asn Phe Pro Pro Asn Gly
            290                 295                 300

Thr His Ser Trp Pro Tyr Trp Asn Gln Gln Leu Val Ala Met Lys Pro
305                 310                 315                 320

Asp Ile Gln Gln Ile Leu Asn Gly Ser Asn Asn Ala
                    325                 330
```

(2) INFORMATION FOR SEQ ID NO:37:

(i) SEQUENCE CHARACTERISTICS:
        (A) LENGTH: 340 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:37:

```
Met Thr Phe Phe Glu Gln Val Arg Arg Leu Arg Ser Ala Ala Thr Thr
 1               5                  10                  15

Leu Pro Arg Arg Val Ala Ile Ala Ala Met Gly Ala Val Leu Val Tyr
            20                  25                  30

Gly Leu Val Gly Thr Phe Gly Gly Pro Ala Thr Ala Gly Ala Phe Ser
            35                  40                  45
```

```
Arg Pro Gly Leu Pro Val Glu Tyr Leu Gln Val Pro Ser Ala Ser Met
 50                  55                  60

Gly Arg Asp Ile Lys Val Gln Phe Gln Gly Gly Pro His Ala Val
 65                  70                  75                  80

Tyr Leu Leu Asp Gly Leu Arg Ala Gln Asp Tyr Asn Gly Trp Asp
                 85                  90                  95

Ile Asn Thr Pro Ala Phe Glu Tyr Tyr Gln Ser Gly Leu Ser Val
            100                 105                 110

Ile Met Pro Val Gly Gln Ser Ser Phe Tyr Thr Asp Trp Tyr Gln
            115                 120                 125

Pro Ser Gln Ser Asn Gly Gln Asn Tyr Thr Tyr Lys Trp Glu Thr Phe
130                 135                 140

Leu Thr Arg Glu Met Pro Ala Trp Leu Gln Ala Asn Lys Gly Val Ser
145                 150                 155                 160

Pro Thr Gly Asn Ala Ala Val Gly Leu Ser Met Ser Gly Gly Ser Ala
                165                 170                 175

Leu Ile Leu Ala Ala Tyr Tyr Pro Gln Gln Phe Pro Tyr Ala Ala Ser
                180                 185                 190

Leu Ser Gly Phe Leu Asn Pro Ser Glu Gly Trp Trp Pro Thr Leu Ile
                195                 200                 205

Gly Leu Ala Met Asn Asp Ser Gly Gly Tyr Asn Ala Asn Ser Met Trp
210                 215                 220

Gly Pro Ser Ser Asp Pro Ala Trp Lys Arg Asn Asp Pro Met Val Gln
225                 230                 235                 240

Ile Pro Arg Leu Val Ala Asn Asn Thr Arg Ile Trp Val Tyr Cys Gly
                245                 250                 255

Asn Gly Thr Pro Ser Asp Leu Gly Gly Asp Asn Ile Pro Ala Lys Phe
                260                 265                 270

Leu Glu Gly Leu Thr Leu Arg Thr Asn Gln Thr Phe Arg Asp Thr Tyr
                275                 280                 285

Ala Ala Asp Gly Gly Arg Asn Gly Val Phe Asn Phe Pro Pro Asn Gly
                290                 295                 300

Thr His Ser Trp Pro Tyr Trp Asn Glu Gln Leu Val Ala Met Lys Ala
305                 310                 315                 320

Asp Ile Gln His Val Leu Asn Gly Ala Thr Pro Pro Ala Ala Pro Ala
                325                 330                 335

Ala Pro Ala Ala
        340

(2) INFORMATION FOR SEQ ID NO:38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:38:

AGCGGCTGGG ACATCAACAC                                             20

(2) INFORMATION FOR SEQ ID NO:39:

(i) SEQUENCE CHARACTERISTICS:
        (A) LENGTH: 20 base pairs
        (B) TYPE: nucleic acid
        (C) STRANDEDNESS: single
```

(D) TOPOLOGY: linear (ii) MOLECULE TYPE: other nucleic acid (xi) SEQUENCE DESCRIPTION: SEQ ID NO:39:

CAGACGCGGG TGTTGTTGGC                                                    20

(2) INFORMATION FOR SEQ ID NO:40:

(i) SEQUENCE CHARACTERISTICS:
        (A) LENGTH: 1211 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

```
GGTACCGGAA GCTGGAGGAT TGACGGTATG AGACTTCTTG ACAGGATTCG TGGGCCTTGG      60
GCACGCCGTT TCGGCGTCGT GGCTGTCGCG ACAGCGATGA TGCCTGCTTT GGTGGGCCTG     120
GCTGGAGGGT CGGCGACCGC CGGAGCATTC TCCCGGCCAG GTCTGCCGGT GGAGTACCTG     180
ATGGTGCCTT CGCCGTCGAT GGGGCGCGAC ATCAAGATCC AGTTCCAGAG CGGTGGCGAG     240
AACTCGCCGG CTCTCTACCT GCTCGACGGC CTGCGTGCGC AGGAGGACTT CAACGGCTGG     300
GACATCAACA CTCAGGCTTT CGAGTGGTTC CTCGACAGCG GCATCTCCGT GGTGATGCCG     360
GTCGGTGGCC AGTCCAGCTT CTACACCGAC TGGTACGCCC CGCCCGTAA CAAGGGCCCG      420
ACCGTGACCT ACAAGTGGGA GACCTTCCTG ACCCAGGAGC TCCCGGGCTG GCTGCAGGCC     480
AACCGCGCGG TCAAGCCGAC CGGCAGCGGC CCTGTCGGTC TGTCGATGGC GGGTTCGGCC     540
GCGCTGAACC TGGCGACCTG GCACCCGGAG CAGTTCATCT ACGCGGGCTC GATGTCCGGC     600
TTCCTGAACC CCTCCGAGGG CTGGTGGCCG TTCCTGATCA ACATCTCGAT GGGTGACGCC     660
GGCGGCTTCA AGGCCGACGA CATGTGGGGC AAGACCGAGG GGATCCCAAC AGCGGTTGGA     720
CAGCGCAACG ATCCGATGCT GAACATCCCG ACCCTGGTCG CCAACAACAC CCGTATCTGG     780
GTCTACTGCG GTAACGGCCA GCCCACCGAG CTCGGCGGCG GCGACCTGCC CGCCACGTTC     840
CTCGAAGGTC TGACCATCCG CACCAACGAG ACCTTCCGCG ACAACTACAT CGCCGCGGGT     900
GGCCACAACG GTGTGTTCAA CTTCCCGGCC AACGGCACGC ACAACTGGGC GTACTGGGGT     960
CGCGAGCTGC AGGCGATGAA GCCTGACCTG CAGGCGCACC TTCTCTGACG GTTGCACGAA    1020
ACGAAGCCCC CGGCCGATTG CGGCCGAGGG TTTCGTCGTC CGGGGCTACT GTGGCCGACA    1080
TAACCGAAAT CAACGCGATG GTGGCTCATC AGGAACGCCG AGGGGGTCAT TGCGCTACGA    1140
CACGAGGTGG GCGAGCAATC CTTCCTGCCC GACGGAGAGG TCAACATCCA CGTCGAGTAC    1200
TCCAGCGTGA A                                                        1211
```

(2) INFORMATION FOR SEQ ID NO:41:

(i) SEQUENCE CHARACTERISTICS:
        (A) LENGTH: 485 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

```
AGCGGCTGGG ACATCAACAC CGCCGCCTTC GAGTGGTACG TCGACTCGGG TCTCGCGGTG      60
ATCATGCCCG TCGGCGGGCA GTCCAGCTTC TACAGCGACT GGTACAGCCC GGCCTGCGGT     120
```

```
AAGGCCGGCT GCCAGACCTA CAAGTGGGAG ACGTTCCTGA CCCAGGAGCT GCCGGCCTAC      180

CTCGCCGCCA ACAAGGGGGT CGACCCGAAC CGCAACGCGG CCGTCGGTCT GTCCATGGCC      240

GGTTCGGCGG CGCTGACGCT GGCGATCTAC CACCCGCAGC AGTTCCAGTA CGCCGGGTCG      300

CTGTCGGGCT ACCTGAACCC GTCCGAGGGG TGGTGGCCGA TGCTGATCAA CATCTCGATG      360

GGTGACGCGG GCGGCTACAA GGCCAACGAC ATGTGGGGTC CACCGAAGGA CCCGAGCAGC      420

GCCTGGAAGC GCAACGACCC GATGGTCAAC ATCGGCAAGC TGGTGGCCAA CAACACCCCC      480

CTCTC                                                                  485

(2) INFORMATION FOR SEQ ID NO:42:

(i) SEQUENCE CHARACTERISTICS:
        (A) LENGTH: 1052 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

GTTGATGAGA AAGGTGGGTT GTTTGCCGTT ATGAAGTTCA CAGAGAAGTG GCGGGGCTCC       60

GCAAAGGCGG CGATGCACCG GGTGGGCGTT GCCGATATGG CCGCCGTTGC GCTGCCCGGA      120

CTGATCGGCT TCGCCGGGGG TTCGGCAACG GCCGGGGCAT TCTCCCGGCC CGGTCTTCCT      180

GTCGAGTACC TCGACGTGTT CTCGCCGTCG ATGGGCCGCG ACATCCGGGT CCAGTTCCAG      240

GGTGGCGGTA CTCATGCGGT CTACCTGCTC GACGGTCTGC GTGCCCAGGA CGACTACAAC      300

GGCTGGGACA TCAACACCCC TGCGTTCGAG TGGTTCTACG AGTCCGGCTT GTCGACGATC      360

ATGCCGGTCG GCGGACAGTC CAGCTTCTAC AGCGACTGGT ACCAGCCGTC TCGGGGCAAC      420

GGGCAGAACT ACACCTACAA GTGGGAGACG TTCCTGACCC AGGAGCTGCC GACGTGGCTG      480

GAGGCCAACC GCGGAGTGTC GCGCACCGGC AACGCGTTCG TCGGCCTGTC GATGGCGGGC      540

AGCGCGGCGC TGACCTACGC GATCCATCAC CCGCAGCAGT TCATCTACGC CTCGTCGCTG      600

TCAGGCTTCC TGAACCCGTC CGAGGGCTGG TGGCCGATGC TGATCGGGCT GGCGATGAAC      660

GACGCAGGCG GCTTCAACGC CGAGAGCATG TGGGGCCCGT CCTCGGACCC GGCGTGGAAG      720

CGCAACGACC CGATGGTCAA CATCAACCAG CTGGTGGCCA ACAACACCCG GATCTGGATC      780

TACTGCGGCA CCGGCACCCC GTCGGAGCTG GACACCGGGA CCCCGGGCCA GAACCTGATG      840

GCCGCGCAGT TCCTCGAAGG ATTCACGTTG CGGACCAACA TCGCCTTCCG TGACAACTAC      900

ATCGCAGCCG GCGGCACCAA CGGTGTCTTC AACTTCCCGG CCTCGGGCAC CCACAGCTGG      960

GGGTACTGGG GCAGCAGCT GCAGCAGATG AAGCCCGACA TCCAGCGGGT TCTGGGAGCT     1020

CAGGCCACCG CCTAGCCACC CACCCCACAC CC                                  1052

(2) INFORMATION FOR SEQ ID NO:43:

(i) SEQUENCE CHARACTERISTICS:
        (A) LENGTH: 326 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:43:

Met Arg Leu Leu Asp Arg Ile Arg Gly Pro Trp Ala Arg Arg Phe Gly
1               5                   10                  15
```

```
Val Val Ala Val Ala Thr Ala Met Met Pro Ala Leu Val Gly Leu Ala
            20                  25                  30

Gly Gly Ser Ala Thr Ala Gly Ala Phe Ser Arg Pro Gly Leu Pro Val
        35                  40                  45

Glu Tyr Leu Met Val Pro Ser Pro Ser Met Gly Arg Asp Ile Lys Ile
50                  55                  60

Gln Phe Gln Ser Gly Gly Glu Asn Ser Pro Ala Leu Tyr Leu Leu Asp
65                  70                  75                  80

Gly Leu Arg Ala Gln Glu Asp Phe Asn Gly Trp Asp Ile Asn Thr Gln
                85                  90                  95

Ala Phe Glu Trp Phe Leu Asp Ser Gly Ile Ser Val Val Met Pro Val
            100                 105                 110

Gly Gly Gln Ser Ser Phe Tyr Thr Asp Trp Tyr Ala Pro Ala Arg Asn
        115                 120                 125

Lys Gly Pro Thr Val Thr Tyr Lys Trp Glu Thr Phe Leu Thr Gln Glu
    130                 135                 140

Leu Pro Gly Trp Leu Gln Ala Asn Arg Ala Val Lys Pro Thr Gly Ser
145                 150                 155                 160

Gly Pro Val Gly Leu Ser Met Ala Gly Ser Ala Ala Leu Asn Leu Ala
                165                 170                 175

Thr Trp His Pro Glu Gln Phe Ile Tyr Ala Gly Ser Met Ser Gly Phe
            180                 185                 190

Leu Asn Pro Ser Glu Gly Trp Trp Pro Phe Leu Ile Asn Ile Ser Met
        195                 200                 205

Gly Asp Ala Gly Phe Lys Ala Asp Asp Met Trp Gly Lys Thr Glu
210                 215                 220

Gly Ile Pro Thr Ala Val Gly Gln Arg Asn Asp Pro Met Leu Asn Ile
225                 230                 235                 240

Pro Thr Leu Val Ala Asn Asn Thr Arg Ile Trp Val Tyr Cys Gly Asn
                245                 250                 255

Gly Gln Pro Thr Glu Leu Gly Gly Asp Leu Pro Ala Thr Phe Leu
        260                 265                 270

Glu Gly Leu Thr Ile Arg Thr Asn Glu Thr Phe Arg Asp Asn Tyr Ile
    275                 280                 285

Ala Ala Gly Gly His Asn Gly Val Phe Asn Phe Pro Ala Asn Gly Thr
290                 295                 300

His Asn Trp Ala Tyr Trp Gly Arg Glu Leu Gln Ala Met Lys Pro Asp
305                 310                 315                 320

Leu Gln Ala His Leu Leu
                325

(2) INFORMATION FOR SEQ ID NO:44:

(i) SEQUENCE CHARACTERISTICS:
        (A) LENGTH: 161 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:44:

Ser Gly Trp Asp Ile Asn Thr Ala Ala Phe Glu Trp Tyr Val Asp Ser
1               5                   10                  15

Gly Leu Ala Val Ile Met Pro Val Gly Gly Gln Ser Ser Phe Tyr Ser
            20                  25                  30
```

```
Asp Trp Tyr Ser Pro Ala Cys Gly Lys Ala Gly Cys Gln Thr Tyr Lys
            35                  40                  45

Trp Glu Thr Phe Leu Thr Gln Glu Leu Pro Ala Tyr Leu Ala Ala Asn
 50                  55                  60

Lys Gly Val Asp Pro Asn Arg Asn Ala Ala Val Gly Leu Ser Met Ala
 65                  70                  75                  80

Gly Ser Ala Ala Leu Thr Leu Ala Ile Tyr His Pro Gln Gln Phe Gln
                 85                  90                  95

Tyr Ala Gly Ser Leu Ser Gly Tyr Leu Asn Pro Ser Glu Gly Trp Trp
                100                 105                 110

Pro Met Leu Ile Asn Ile Ser Met Gly Asp Ala Gly Gly Tyr Lys Ala
                115                 120                 125

Asn Asp Met Trp Gly Pro Pro Lys Asp Pro Ser Ser Ala Trp Lys Arg
130                 135                 140

Asn Asp Pro Met Val Asn Ile Gly Lys Leu Val Ala Asn Asn Thr Pro
145                 150                 155                 160

Leu
```

(2) INFORMATION FOR SEQ ID NO:45:

(i) SEQUENCE CHARACTERISTICS:
        (A) LENGTH: 334 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:45:

```
Met Lys Phe Thr Glu Lys Trp Arg Gly Ser Ala Lys Ala Ala Met His
 1                   5                  10                  15

Arg Val Gly Val Ala Asp Met Ala Ala Val Ala Leu Pro Gly Leu Ile
                 20                  25                  30

Gly Phe Ala Gly Gly Ser Ala Thr Ala Gly Ala Phe Ser Arg Pro Gly
                 35                  40                  45

Leu Pro Val Glu Tyr Leu Asp Val Phe Ser Pro Ser Met Gly Arg Asp
 50                  55                  60

Ile Arg Val Gln Phe Gln Gly Gly Gly Thr His Ala Val Tyr Leu Leu
 65                  70                  75                  80

Asp Gly Leu Arg Ala Gln Asp Asp Tyr Asn Gly Trp Asp Ile Asn Thr
                 85                  90                  95

Pro Ala Phe Glu Trp Phe Tyr Glu Ser Gly Leu Ser Thr Ile Met Pro
                100                 105                 110

Val Gly Gly Gln Ser Ser Phe Tyr Ser Asp Trp Tyr Gln Pro Ser Arg
                115                 120                 125

Gly Asn Gly Gln Asn Tyr Thr Tyr Lys Trp Glu Thr Phe Leu Thr Gln
130                 135                 140

Glu Leu Pro Thr Trp Leu Glu Asn Arg Gly Val Ser Arg Thr Gly
145                 150                 155                 160

Asn Ala Phe Val Gly Leu Ser Met Ala Gly Ser Ala Ala Leu Thr Tyr
                165                 170                 175

Ala Ile His His Pro Gln Gln Phe Ile Tyr Ala Ser Ser Leu Ser Gly
                180                 185                 190

Phe Leu Asn Pro Ser Glu Gly Trp Trp Pro Met Leu Ile Gly Leu Ala
                195                 200                 205
```

```
Met Asn Asp Ala Gly Gly Phe Asn Ala Glu Ser Met Trp Gly Pro Ser
    210                 215                 220

Ser Asp Pro Ala Trp Lys Arg Asn Asp Pro Met Val Asn Ile Asn Gln
225                 230                 235                 240

Leu Val Ala Asn Asn Thr Arg Ile Trp Ile Tyr Cys Gly Thr Gly Thr
                245                 250                 255

Pro Ser Glu Leu Asp Thr Gly Thr Pro Gly Gln Asn Leu Met Ala Ala
            260                 265                 270

Gln Phe Leu Glu Gly Phe Thr Leu Arg Thr Asn Ile Ala Phe Arg Asp
        275                 280                 285

Asn Tyr Ile Ala Ala Gly Gly Thr Asn Gly Val Phe Asn Phe Pro Ala
    290                 295                 300

Ser Gly Thr His Ser Trp Gly Tyr Trp Gly Gln Gln Leu Gln Gln Met
305                 310                 315                 320

Lys Pro Asp Ile Gln Arg Val Leu Gly Ala Gln Ala Thr Ala
                325                 330
```

(2) INFORMATION FOR SEQ ID NO:46:

(i) SEQUENCE CHARACTERISTICS:
        (A) LENGTH: 795 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:46:

```
CTGCCGCGGG TTTGCCATCT CTTGGGTCCT GGGTCGGGAG GCCATGTTCT GGGTAACGAT     60
CCGGTACCGT CCGGCGATGT GACCAACATG CGAACAGCGA CAACGAAGCT AGGAGCGGCG    120
CTCGGCGCAG CAGCATTGGT GGCCGCCACG GGGATGGTCA GCGCGGCGAC GGCGAACGCC    180
CAGGAAGGGC ACCAGGTCCG TTACACGCTC ACCTCGGCCG GCGCTTACGA GTTCGACCTG    240
TTCTATCTGA CGACGCAGCC GCCGAGCATG CAGGCGTTCA ACGCCGACGC GTATGCGTTC    300
GCCAAGCGGG AGAAGGTCAG CCTCGCCCCG GGTGTGCCGT GGGTCTTCGA AACCACGATG    360
GCCGACCCGA ACTGGGCGAT CCTTCAGGTC AGCAGCACCA CCCGCGGTGG GCAGGCCGCC    420
CCGAACGCGC ACTGCGACAT CGCCGTCGAT GGCCAGGAGG TGCTCAGCCA GCACGACGAC    480
CCCTACAACG TGCGGTGCCA GCTCGGTCAG TGGTGAGTCA CCTCGCCGAG AGTCCGGCCA    540
GCGCCGGCGG CAGCGGCTCG CGGTGCAGCA CCCCGAGGCG CTGGGTCGCG CGGGTCAGCG    600
CGACGTAAAG ATCGCTGGCC CCGCGCGGCC CCTCGGCGAG GATCTGCTCC GGGTAGACCA    660
CCAGCACGGC GTCTAACTCC AGACCCTTGG TCTGCGTGGG TGCCACCGCG CCCGGGACAC    720
CGGGCGGGCC GATCACCACG CTGGTGCCCT CCCGGTCCGC CTCCGCACGC ACGAAATCGT    780
CGATGGCACC GGCGA                                                     795
```

(2) INFORMATION FOR SEQ ID NO:47:

(i) SEQUENCE CHARACTERISTICS:
        (A) LENGTH: 142 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:47:

Met Arg Thr Ala Thr Thr Lys Leu Gly Ala Ala Leu Gly Ala Ala Ala

```
1               5                    10                   15
Leu Val Ala Ala Thr Gly Met Val Ser Ala Ala Thr Ala Asn Ala Gln
                 20                  25                  30
Glu Gly His Gln Val Arg Tyr Thr Leu Thr Ser Ala Gly Ala Tyr Glu
             35                  40                  45
Phe Asp Leu Phe Tyr Leu Thr Thr Gln Pro Pro Ser Met Gln Ala Phe
         50                  55                  60
Asn Ala Asp Ala Tyr Ala Phe Ala Lys Arg Glu Lys Val Ser Leu Ala
 65                  70                  75                  80
Pro Gly Val Pro Trp Val Phe Glu Thr Thr Met Ala Asp Pro Asn Trp
                 85                  90                  95
Ala Ile Leu Gln Val Ser Ser Thr Thr Arg Gly Gly Gln Ala Ala Pro
             100                 105                 110
Asn Ala His Cys Asp Ile Ala Val Asp Gly Gln Glu Val Leu Ser Gln
             115                 120                 125
His Asp Asp Pro Tyr Asn Val Arg Cys Gln Leu Gly Gln Trp
         130                 135                 140
```

(2) INFORMATION FOR SEQ ID NO:48:

(i) SEQUENCE CHARACTERISTICS:
        (A) LENGTH: 300 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:48:

```
GCCAGTGCGC CAACGGTTTT CATCGATGCC GCACACAACC CCGGTGGGCC CTGCGCTTGC      60
CGAAGGCTGC GCGACGAGTT CGACTTCCGG TATCTCGTCG GCGTCGTCTC GGTGATGGGG     120
GACAAGGACG TGGACGGGAT CCGCCAGGAC CCGGGCGTGC GGACGGGCG  CGGTCTCGCA     180
CTGTTCGTCT CGGGCGACAA CCTTCGAAAG GGTGCGGCGC TCAACACGAT CCAGATCGCC     240
GAGCTGCTGG CCGCCCAGTT GTAAGTGTTC CGCCGAAATT GCATTCCACG CCGATAATCG     300
```

(2) INFORMATION FOR SEQ ID NO:49:

(i) SEQUENCE CHARACTERISTICS:
        (A) LENGTH: 563 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:49:

```
GGATCCTCGG CCGGCTCAAG AGTCCGCGCC GAGGTGGATG TGACGCTGGA CGGCTACGAG      60
TTCAGTCGGG CCTGCGAGGC GCTGTACCAC TTCGCCTGGG ACGAGTTCTG CGACTGGTAT     120
GTCGAGCTTG CCAAAGTGCA ACTGGGTGAA GGTTTCTCGC ACACCACGGC CGTGTTGGCC     180
ACCGTGCTCG ATGTGCTGCT CAAGCTTCTG CACCCGGTCA TGCCGTTCGT CACCGAGGTG     240
CTGTGGAAGG CCCTGACCGG GCGGGCCGGC GCGAGCGAAC GTCTGGGAAA TGTGGAGTCA     300
CTGGTCGTCG CGGACTGGCC CACGCCCACC GGATACGCGC TGGATCAGGC TGCCGCACAA     360
CGGATCGCCG ACACCCAGAA GTTGATCACC GAGGTGCGCC GGTTCCGCAG CGATCAGGGT     420
CTGGCCGACC GCCAGCGGGT GCCTGCCCGG TTGTCCGGCA TCGACACCGC GGGTCTGGAC     480
GCCCATGTCC CGGCGGTGCG CGCGCTGGCC TGGCTTGACC GAGGGTGATG AGGGCTTCAC     540
```

CGCGTCCGAA TCGGTCGAGG TGC                                                      563

(2) INFORMATION FOR SEQ ID NO:50:

(i) SEQUENCE CHARACTERISTICS:
        (A) LENGTH: 434 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

GGGCCGGGCC CGAGGATGAG CAAGTTCGAA GTCGTCACCG GGATGGCGTT CGCGGCTTTC      60

GCCGACGCGC CCATCGACGT CGCCGTCGTC GAGGTCGGGC TCGGTGGTCG CTGGGACGCG     120

ACGAACGTGG TGAACGCACC GGTCGCGGTC ATCACCCCGA TCGGGGTGGA CCACACCGAC     180

TACCTCGGTG ACACGATCGC CGAGATCGCC GGGGAGAAGG CCGGAAATCA TCACCCGCCA     240

GCCGACGACC TGGTGCCGAC CGACACCGTC GCCGTGCTGG CGCGGCAGGT TCCCGAGGCC     300

ATGGAGGTGC TGCTGGCCCA GGCGGTGCGC TCGGATGCGG CTGTAGCGCG CGAGGATTCG     360

GAGTGCGCGG TGCTGGGCCG TCAGGTCGCC ATCGGCGGCA GCTGCTCCGG TTGCAGGGGC     420

TCGGTGGCGT CTAC                                                      434

(2) INFORMATION FOR SEQ ID NO:51:

(i) SEQUENCE CHARACTERISTICS:
        (A) LENGTH: 438 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:51:

GGATCCCACT CCCGCGCCGG CGGCGGCCAG CTGGTACGGC CATTCCAGCG TGCTGATCGA      60

GGTCGACGGC TACCGCGTGC TGGCCGACCC GGTGTGGAGC AACAGATGTT CGCCCTCACG     120

GGCGGTCGGA CCGCAGCGCA TGCACGACGT CCCGGTGCCG CTGGAGGCGC TTCCCGCCGT     180

GGACGCGGTG GTGATCGCCA ACGACCACTA CGACCACCTC GACATCGACA CCATCGTCGC     240

GTTGGCGCAC ACCCAGCGGG CCCCGTTCGT GGTGCCGTTG GGCATCGGCG CACACCTGCG     300

CAAGTGGGGC GTCCCCGAGG CGCGGATCGT CGAGTTGGAC TGGCACGAAG CCCACCGCAT     360

CGACGACCTG ACGCTGGTCT GCACCCCCGC CCGGCACTTC TCCGGCCGGT TGTTCTCCCG     420

CGACTCGACG CTGTGGGC                                                  438

(2) INFORMATION FOR SEQ ID NO:52:

(i) SEQUENCE CHARACTERISTICS:
        (A) LENGTH: 87 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:52:

Ala Ser Ala Pro Thr Val Phe Ile Asp Ala Ala His Asn Pro Gly Gly
1               5                   10                  15

Pro Cys Ala Cys Arg Arg Leu Arg Asp Glu Phe Asp Phe Arg Tyr Leu
            20                  25                  30

Val Gly Val Val Ser Val Met Gly Asp Lys Asp Val Asp Gly Ile Arg
            35                  40                  45

Gln Asp Pro Gly Val Pro Asp Gly Arg Gly Leu Ala Leu Phe Val Ser
        50                  55                  60

Gly Asp Asn Leu Arg Lys Gly Ala Ala Leu Asn Thr Ile Gln Ile Ala
65                  70                  75                  80

Glu Leu Leu Ala Ala Gln Leu
                85

(2) INFORMATION FOR SEQ ID NO:53:

(i) SEQUENCE CHARACTERISTICS:
        (A) LENGTH: 175 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:53:

Gly Ser Ser Ala Gly Ser Arg Val Arg Ala Glu Val Asp Val Thr Leu
1               5                   10                  15

Asp Gly Tyr Glu Phe Ser Arg Ala Cys Glu Ala Leu Tyr His Phe Ala
            20                  25                  30

Trp Asp Glu Phe Cys Asp Trp Tyr Val Glu Leu Ala Lys Val Gln Leu
            35                  40                  45

Gly Glu Gly Phe Ser His Thr Thr Ala Val Leu Ala Thr Val Leu Asp
        50                  55                  60

Val Leu Leu Lys Leu Leu His Pro Val Met Pro Phe Val Thr Glu Val
65                  70                  75                  80

Leu Trp Lys Ala Leu Thr Gly Arg Ala Gly Ala Ser Glu Arg Leu Gly
                85                  90                  95

Asn Val Glu Ser Leu Val Val Ala Asp Trp Pro Thr Pro Thr Gly Tyr
            100                 105                 110

Ala Leu Asp Gln Ala Ala Ala Gln Arg Ile Ala Asp Thr Gln Lys Leu
            115                 120                 125

Ile Thr Glu Val Arg Arg Phe Arg Ser Asp Gln Gly Leu Ala Asp Arg
        130                 135                 140

Gln Arg Val Pro Ala Arg Leu Ser Gly Ile Asp Thr Ala Gly Leu Asp
145                 150                 155                 160

Ala His Val Pro Ala Val Arg Ala Leu Ala Trp Leu Asp Arg Gly
                165                 170                 175

(2) INFORMATION FOR SEQ ID NO:54:

(i) SEQUENCE CHARACTERISTICS:
        (A) LENGTH: 144 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:54:

Gly Pro Gly Pro Arg Asn Ser Lys Phe Glu Val Val Thr Gly Met Ala
1               5                   10                  15

Phe Ala Ala Phe Ala Asp Ala Pro Ile Asp Val Ala Val Val Glu Val
            20                  25                  30

Gly Leu Gly Gly Arg Trp Asp Ala Thr Asn Val Val Asn Ala Pro Val

```
                    35                  40                  45
Ala Val Ile Thr Pro Ile Gly Val Asp His Thr Asp Tyr Leu Gly Asp
                50                  55                  60
Thr Ile Ala Glu Ile Ala Gly Glu Lys Ala Gly Asn His His Pro Pro
65                  70                  75                  80
Ala Asp Asp Leu Val Pro Thr Asp Thr Val Ala Val Leu Ala Arg Gln
                85                  90                  95
Val Pro Glu Ala Asn Glu Val Leu Leu Ala Gln Ala Val Arg Ser Asp
                100                 105                 110
Ala Ala Val Ala Arg Glu Asp Ser Glu Cys Ala Val Leu Gly Arg Gln
                115                 120                 125
Val Ala Ile Gly Gly Ser Cys Ser Gly Cys Arg Gly Ser Val Ala Ser
                130                 135                 140

(2) INFORMATION FOR SEQ ID NO:55:

(i) SEQUENCE CHARACTERISTICS:
        (A) LENGTH: 145 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:55:

Asp Pro Thr Pro Ala Pro Ala Ala Ala Ser Trp Tyr Gly His Ser Ser
1               5                   10                  15
Val Leu Ile Glu Val Asp Gly Tyr Arg Val Leu Ala Asp Pro Val Trp
                20                  25                  30
Ser Asn Arg Cys Ser Pro Ser Arg Ala Val Gly Pro Gln Arg Met His
                35                  40                  45
Asp Val Pro Val Pro Leu Glu Ala Leu Pro Ala Val Asp Ala Val Val
                50                  55                  60
Ile Ser Asn Asp His Tyr Asp His Leu Asp Ile Asp Thr Ile Val Ala
65                  70                  75                  80
Leu Ala His Thr Gln Arg Ala Pro Phe Val Val Pro Leu Gly Ile Gly
                85                  90                  95
Ala His Leu Arg Lys Trp Gly Val Pro Glu Ala Arg Ile Val Glu Leu
                100                 105                 110
Asp Trp His Glu Ala His Arg Ile Asp Asp Leu Thr Leu Val Cys Thr
                115                 120                 125
Pro Ala Arg His Phe Ser Gly Arg Leu Phe Ser Arg Asp Ser Thr Leu
                130                 135                 140
Trp
145
```

COMPOUNDS AND METHODS FOR TREATMENT AND DIAGNOSIS OF MYCOBACTERIAL INFECTIONS

TECHNICAL FIELD

The present invention relates generally to the detection, treatment and prevention of infectious diseases. In particular, the invention is related to compounds and methods for the treatment of mycobacterial infections including *Mycobacterium tuberculosis* and *Mycobacterium avium*. The invention is further related to compounds that function as non-specific immune response amplifiers, and the use of such non-specific immune response amplifiers as adjuvants in vaccination or immunotherapy against infectious disease, and in certain treatments for immune disorders and cancer.

BACKGROUND OF THE INVENTION

Tuberculosis is a chronic, infectious disease, that is caused by infection with *Mycobacterium tuberculosis* (*M. tuberculosis*). It is a major disease in developing countries, as well as an increasing problem in developed areas of the world, with about 8 million new cases and 3 million deaths each year. Although the infection may be asymptomatic for a considerable period of time, the disease is most commonly manifested as a chronic inflammation of the lungs, resulting in fever and respiratory symptoms. If left untreated, significant morbidity and death may result.

Although tuberculosis can generally be controlled using extended antibiotic therapy, such treatment is not sufficient to prevent the spread of the disease. Infected individuals may be asymptomatic, but contagious, for some time. In addition, although compliance with the treatment regimen is critical, patient behavior is difficult to monitor. Some patients do not complete the course of treatment, which can lead to ineffective treatment and the development of drug resistant mycobacteria.

Inhibiting the spread of tuberculosis requires effective vaccination and accurate, early diagnosis of the disease. Currently, vaccination with live bacteria is the most efficient method for inducing protective immunity. The most common mycobacterium employed for this purpose is Bacillus Calmette-Guerin (BCG), an avirulent strain of *Mycobacterium bovis*. However, the safety and efficacy of BCG is a source of controversy and some countries, such as the United States, do not vaccinate the general public. Diagnosis of *M. tuberculosis* infection is commonly achieved using a skin test, which involves intradermal exposure to tuberculin PPD (protein-purified derivative). Antigen-specific T cell responses result in measurable induration at the injection site by 48–72 hours after injection, thereby indicating exposure to mycobacterial antigens. Sensitivity and specificity have, however, been a problem with this test, and individuals vaccinated with BCG cannot be distinguished from infected individuals.

A less well-known mycobacterium that has been used for immunotherapy for tuberculosis, and also leprosy, is *Mycobacterium vaccae*, which is non-pathogenic in humans. However, there is less information on the efficacy of *M. vaccae* compared with BCG, and it has not been used widely to vaccinate the general public. *M. bovis* BCG and *M. vaccae* are believed to contain antigenic compounds that are recognized by the immune system of individuals exposed to infection with *M tuberculosis*.

There thus remains a need in the art for effective compounds and methods for preventing, treating and detecting tuberculosis.

SUMMARY OF THE INVENTION

Briefly stated, the present invention provides compounds and methods for the prevention, treatment and diagnosis of mycobacterial infection, together with adjuvants for use in vaccines or immunotherapy of infectious diseases and cancers.

In a first aspect, polypeptides derived from *Mycobacterium vaccae* are provided comprising an immunogenic portion of a soluble antigen, or a variant of such an antigen. In one embodiment, the soluble antigen induces an immune response in patients previously exposed to a mycobacterium. In a second embodiment, the soluble antigen includes an amino acid sequence selected from the group consisting of sequences recited in SEQ ID NOS: 4–29, 43–45, 47 and 52–55, and variants thereof.

In another embodiment, the antigen comprises an amino acid sequence encoded by a DNA molecule selected from the group consisting of: sequences recited in SEQ ID NOS: 40–42, 46 and 48–51, and variants thereof; and the complements of said sequences and variants of such complements.

DNA sequences encoding the inventive polypeptides, expression vectors comprising these DNA sequences, and host cells transformed or transfected with such expression vectors are also provided.

In another aspect, the present invention provides fusion proteins comprising a first and a second inventive polypeptide or, alternatively, an inventive polypeptide and a known *M. tuberculosis* antigen.

Within other aspects, the present invention provides pharmaceutical compositions that comprise at least one of the inventive polypeptides, or a DNA molecule encoding such a polypeptide, and a physiologically acceptable carrier. The invention also provides vaccines comprising at least one of the above polypeptides and a non-specific immune response amplifier, together with vaccines comprising at least one DNA sequence encoding such polypeptides and a non-specific immune response amplifier.

In yet another aspect, methods are provided for inducing protective immunity in a patient, comprising administering to a patient an effective amount of one or more of the above polypeptides together with an immune response amplifier.

In further aspects of this invention, methods and diagnostic kits are provided for detecting tuberculosis in a patient. In a first embodiment, the method comprises contacting dermal cells of a patient with one or more of the above polypeptides and detecting an immune response on the patient's skin. In a second embodiment, the method comprises contacting a biological sample with at least one of the above polypeptides; and detecting in the sample the presence of antibodies that bind to the polypeptide or polypeptides, thereby detecting *M. tuberculosis* infection in the biological sample. Suitable biological samples include whole blood, sputum, serum, plasma, saliva, cerebrospinal fluid and urine.

Diagnostic kits comprising one or more of the above polypeptides in combination with an apparatus sufficient to contact the polypeptide with the dermal cells of a patient are provided. The present invention also provides diagnostic kits comprising one or more of the inventive polypeptides in combination with a detection reagent.

In yet another aspect, the present invention provides antibodies, both polyclonal and monoclonal, that bind to the polypeptides described above, as well as methods for their use in the detection of *M. tuberculosis* infection.

The present invention also provides methods for enhancing a non-specific immune response to an antigen, comprising administering *M. vaccae* culture filtrate or delipidated *M. vaccae* cells.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 3 is a comparison of the Antigen 85A protein sequence obtained from M. vaccae with those from M. bovis (SEQ ID NO: 34) M. tuberculosis (SEQ ID NO: 32) and M. leprae (SEQ ID NO: 30).

FIG. 4C(ii) illustrates the non-specific immune amplifying effects of delipidated M. vaccae from which glycolipids had been removed and the proteins extracted with SDS. FIG. 4C(iii) illustrates that the adjuvant effect of the preparation of FIG. 4C(ii) is destroyed by treatment with the proteolytic enzyme pronase. FIG. 4D illustrates the non-specific immune amplifying effects of heat-killed M. vaccae (FIG. 4D(i)), M. tuberculosis (FIG. 4D(ii)), M. bovis BCG (FIG. 4D(iii)), M. phlei (FIG. 4D(iv)) and M. smegmatis (FIG. 4D(v)).

DETAILED DESCRIPTION OF THE INVENTION

Figure 1A:
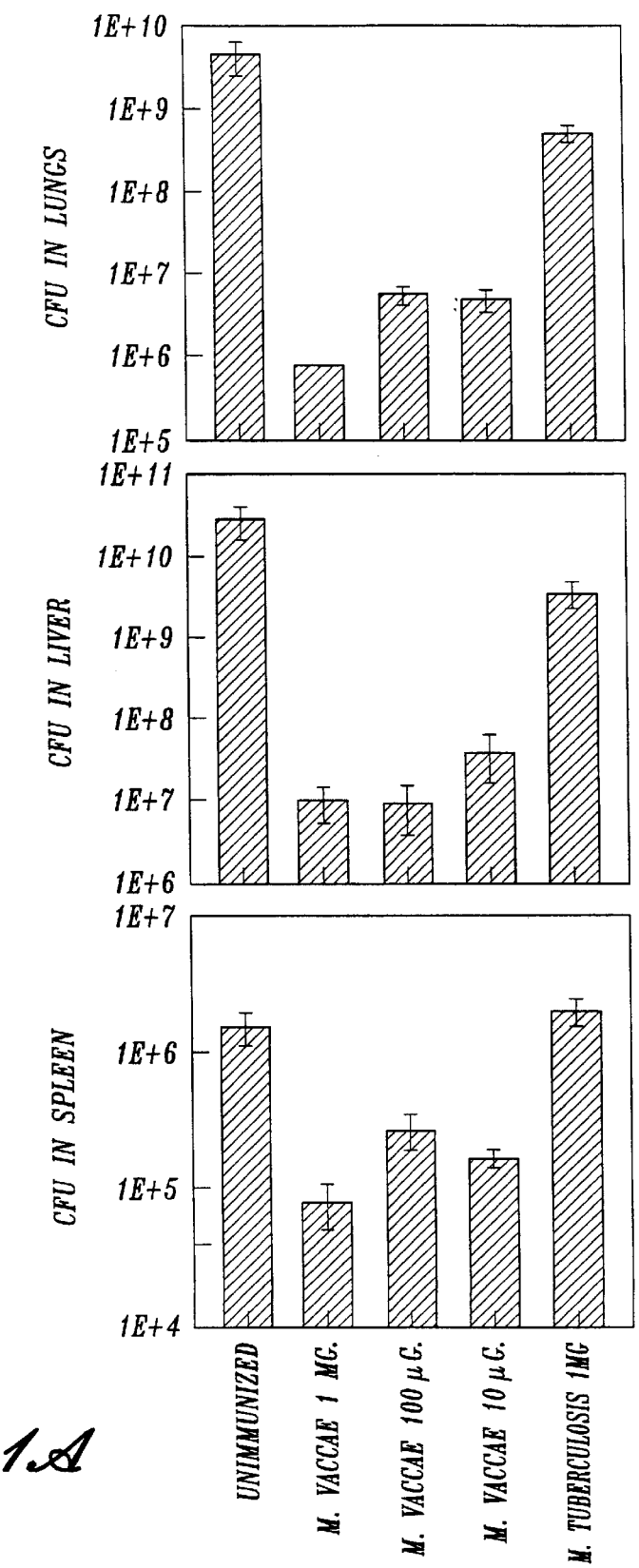
FIGS. 1A and 1B illustrate the protective effects of immunizing mice with autoclaved M. vaccae or unfractionated M. vaccae culture filtrates, respectively, prior to infection with live M. tuberculosis H37Rv.

As noted above, the present invention is generally directed to compositions and methods for preventing, treating and diagnosing mycobacterial infections, including M. tuberculosis and M. avium infections.

Considerable research efforts have been directed towards elucidating the mechanism of immune response to mycobacterial infection, in particular M. tuberculosis infection. While macrophages have been shown to act as the principal effectors of M. tuberculosis immunity, T cells are the predominant inducers of such immunity. The essential role of T cells in protection against M. tuberculosis infection is illustrated by the frequent occurrence of M. tuberculosis in AIDS patients, due to the depletion of CD4 T cells associated with human immunodeficiency virus (HIV) infection. Mycobacterium-reactive CD4 T cells have been shown to be potent producers of gamma-interferon (IFN-γ), which, in turn, has been shown to trigger the anti-mycobacterial effects of macrophages in mice. While the role of IFN-γ in humans is less clear, studies have shown that 1,25-dihydroxy-vitamin D3, either alone or in combination with IFN-γ or tumor necrosis factor-alpha, activates human macrophages to inhibit M. tuberculosis infection. Furthermore, it is known that IFN-γ stimulates human macrophages to make 1,25-dihydroxy-vitamin D3. Similarly, IL-12 has been shown to play a role in stimulating resistance to M. tuberculosis infection. Another property of CD4+ T cells and macrophages is their ability to activate CD8+ cytotoxic T cells which are capable of killing pathogen-infected cells. CD8+ T cells have been shown to kill macrophages and other cells that harbour M. tuberculosis. For a review of the immunology of M. tuberculosis infection see Chan and Kaufmann in Tuberculosis: Pathogenesis, Protection and Control, Bloom (ed.), ASM Press, Washington, D.C., 1994.

The compositions of the present invention include polypeptides that comprise at least one immunogenic portion of a soluble M. vaccae antigen, or a variant thereof. Such polypeptides stimulate T cell proliferation, and/or, interferon gamma secretion from T cells of individuals exposed to M. tuberculosis. A "soluble M. vaccae antigen" is a protein of M. vaccae origin that is present in M. vaccae culture filtrate. As used herein, the term "polypeptide" encompasses amino acid chains of any length, including full length proteins (i.e., antigens), wherein the amino acid residues are linked by covalent peptide bonds. Thus, a polypeptide comprising an immunogenic portion of one of the above antigens may consist entirely of the immunogenic portion, or may contain additional sequences. The additional sequences may be derived from the native M. vaccae antigen or may be heterologous, and such sequences may (but need not) be immunogenic.

"Immunogenic," as used herein, refers to the ability to elicit an immune response in a patient, such as a human, or in a biological sample. In particular, immunogenic antigens are capable of stimulating cell proliferation, interleukin-12 production or interferon-γ production in biological samples comprising one or more cells selected from the group of T cells, NK cells, B cells and macrophages, where the cells are derived from an M. tuberculosis-immune individual. Polypeptides comprising at least an immunogenic portion of one or more M. vaccae antigens may generally be used to detect tuberculosis or to induce protective immunity against tuberculosis in a patient.

The compositions and methods of this invention also encompass variants of the above polypeptides. As used herein, the term "variant" covers any sequence which has at least about a 99% probability of being the same as the inventive sequence. The probability for DNA sequences is measured by FASTA (version 2.0u4, February 1996; Pearson W. R. et al., Proc. Natl. Acad. Sci., 85:2444–2448, 1988), the probability for translated DNA sequences is measured by TBLASTX and that for protein sequences is measured by BLASTP (Altschul, S. F. et al. J. Mol. Biol., 215:403–410, 1990). The term "variants" thus encompasses sequences wherein the probability of finding a match by chance (smallest sum probability), is less than about 1% as measured by any of the above tests.

A polypeptide of the present invention may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

In general, M. vaccae antigens, and DNA sequences encoding such antigens, may be prepared using any of a variety of procedures. For example, soluble antigens may be isolated from M. vaccae culture filtrate as described below. Antigens may also be produced recombinantly by inserting a DNA sequence that encodes the antigen into an expression vector and expressing the antigen in an appropriate host. Any of a variety of expression vectors known to those of ordinary skill in the art may be employed. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line such as COS or CHO. The DNA sequences expressed in this manner may encode naturally occurring antigens, portions of naturally occurring antigens, or other variants thereof.

DNA sequences encoding *M. vaccae* antigens may be obtained by screening an appropriate *M. vaccae* cDNA or genomic DNA library for DNA sequences that hybridize to degenerate oligonucleotides derived from partial amino acid sequences of isolated soluble antigens. Suitable degenerate oligonucleotides may be designed and synthesized, and the screen may be performed as described, for example in Maniatis et al., *Molecular Cloning: A Laboratory Manual*, Cold Spring Harbor Laboratories, Cold Spring Harbor, N.Y., 1989. As described below, polymerase chain reaction (PCR) may be employed to isolate a nucleic acid probe from a cDNA or genomic DNA library. The library screen may then be performed using the isolated probe.

DNA molecules encoding *M. vaccae* antigens may also be isolated by screening an appropriate *M. vaccae* expression library with anti-sera (e.g., rabbit or monkey) raised specifically against *M. vaccae* antigens.

Regardless of the method of preparation, the antigens described herein have the ability to induce an immunogenic response. More specifically, the antigens have the ability to induce cell proliferation and/or cytokine production (for example, interferon-γ and/or interleukin-12 production) in T cells, NK cells, B cells or macrophages derived from an *M. tuberculosis*-immune individual. An *M. tuberculosis*-immune individual is one who is considered to be resistant to the development of tuberculosis by virtue of having mounted an effective T cell response to *M. tuberculosis*. Such individuals may be identified based on a strongly positive (i.e., greater than about 10 mm diameter induration) intradermal skin test response to tuberculosis proteins (PPD), and an absence of any symptoms of tuberculosis infection.

The selection of cell type for use in evaluating an immunogenic response to an antigen will depend on the desired response. For example, interleukin-12 production is most readily evaluated using preparations containing B cells or macrophages. T cells, NK cells, B cells and macrophages derived from *M. tuberculosis*-immune individuals may be prepared using methods well known in the art. For example, a preparation of peripheral blood mononuclear cells (PBMCs) may be employed without further separation of component cells. PBMCs may be prepared, for example, using density centrifugation through Ficoll™ (Winthrop Laboratories, N.Y.). T cells for use in the assays described herein may be purified directly from PBMCs. Alternatively, an enriched T cell line reactive against mycobacterial proteins, or T cell clones reactive to individual mycobacterial proteins, may be employed. Such T cell clones may be generated by, for example, culturing PBMCs from *M. tuberculosis*-immune individuals with mycobacterial proteins for a period of 2–4 weeks. This allows expansion of only the mycobacterial protein-specific T cells, resulting in a line composed solely of such cells. These cells may then be cloned and tested with individual proteins, using methods well known in the art, to more accurately define individual T cell specificity. Assays for cell proliferation or cytokine production in T cells, NK cells, B cells or macrophages may be performed, for example, using the procedures described below.

In general, immunogenic antigens are those antigens that stimulate proliferation or cytokine production (i.e., interferon-γ and/or interleukin-12 production) in T cells, NK cells, B cells or macrophages derived from at least about 25% of *M. tuberculosis*-immune individuals. Among these immunogenic antigens, polypeptides having superior therapeutic properties may be distinguished based on the magnitude of the responses in the above assays and based on the percentage of individuals for which a response is observed. In addition, antigens having superior therapeutic properties will not stimulate cell proliferation or cytokine production in vitro in cells derived from more than about 25% of individuals that are not *M. tuberculosis*-immune, thereby eliminating responses that are not specifically due to *M. tuberculosis*-responsive cells. Thus, those antigens that induce a response in a high percentage of T cell, NK cell, B cell or macrophage preparations from *M. tuberculosis*-immune individuals (with a low incidence of responses in cell preparations from other individuals) have superior therapeutic properties.

Antigens with superior therapeutic properties may also be identified based on their ability to diminish the severity of *M. tuberculosis* infection, or other mycobacterial infection, in experimental animals, when administered as a vaccine. Suitable vaccine preparations for use in experimental animals are described in detail below.

Antigens having superior diagnostic properties may generally be identified based on the ability to elicit a response in an intradermal skin test performed on an individual with active tuberculosis, but not in a test performed on an individual who is not infected with *M. tuberculosis*. Skin tests may generally be performed as described below, with a response of at least about 5 mm induration considered positive.

Immunogenic portions of the antigens described herein may be prepared and identified using well known techniques, such as those summarized in Paul, *Fundamental Immunology*, 3d ed., Raven Press, 1993, pp. 243–247. Such techniques include screening polypeptide portions of the native antigen for immunogenic properties. The representative proliferation and cytokine production assays described herein may be employed in these screens. An immunogenic portion of a polypeptide is a portion that, within such representative assays, generates an immune response (e.g., cell proliferation, interferon-γ production or interleukin-12 production) that is substantially similar to that generated by the full length antigen. In other words, an immunogenic portion of an antigen may generate at least about 20%, preferably about 65%, and most preferably about 100%, of the proliferation induced by the full length antigen in the model proliferation assay described herein. An immunogenic portion may also, or alternatively, stimulate the production of at least about 20%, preferably about 65% and most preferably about 100%, of the interferon-γ and/or interleukin-12 induced by the full length antigen in the model assay described herein.

Portions and other variants of *M. vaccae* antigens may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems, Inc. (Foster City, Calif.), and may be operated according to the manufacturer's instructions. Variants of a native antigen may be prepared using standard mutagenesis techniques, such as oligonucleotide-directed site-specific mutagenesis. Sections of the DNA sequence may also be removed using standard techniques to permit preparation of truncated polypeptides.

In general, regardless of the method of preparation, the polypeptides disclosed herein are prepared in substantially pure form. Preferably, the polypeptides are at least about 80% pure, more preferably at least about 90% pure and most preferably at least about 99% pure. In certain preferred embodiments, described in detail below, the substantially pure polypeptides are incorporated into pharmaceutical compositions or vaccines for use in one or more of the methods disclosed herein.

The present invention also provides fusion proteins comprising a first and a second inventive polypeptide or, alternatively, a polypeptide of the present invention and a known *M. tuberculosis* antigen, such as the 38 kD antigen described in Andersen and Hansen, *Infect. Immun.* 57:2481–2488, 1989, together with variants of such fusion proteins. The fusion proteins of the present invention may also include a linker peptide between the first and second polypeptides.

A DNA sequence encoding a fusion protein of the present invention is constructed using known recombinant DNA techniques to assemble separate DNA sequences encoding the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may be from 1 to about 50 amino acids in length. Peptide linker sequences are not required when the first and second polypeptides have non-essential N-terminal amino acid regions that can be used to separate the functional domains and prevent steric interference.

The ligated DNA sequences encoding the fusion proteins are cloned into suitable expression systems using techniques known to those of ordinary skill in the art.

In another aspect, the present invention provides methods for using one or more of the inventive polypeptides or fusion proteins (or DNA molecules encoding such polypeptides or fusion proteins) to induce protective immunity against tuberculosis in a patient. As used herein, a "patient" refers to any warm-blooded animal, preferably a human. A patient may be afflicted with a disease, or may be free of detectable disease or infection. In other words, protective immunity may be induced to prevent or treat tuberculosis.

In this aspect, the polypeptide, fusion protein or DNA molecule is generally present within a pharmaceutical composition or a vaccine. Pharmaceutical compositions may comprise one or more polypeptides, each of which may contain one or more of the above sequences (or variants thereof), and a physiologically acceptable carrier. Vaccines may comprise one or more of the above polypeptides and a non-specific immune response amplifier, such as an adjuvant or a liposome, into which the polypeptide is incorporated. Such pharmaceutical compositions and vaccines may also contain other mycobacterial antigens, either, as discussed above, incorporated into a fusion protein or present within a separate polypeptide.

Alternatively, a vaccine of the present invention may contain DNA encoding one or more polypeptides as described above, such that the polypeptide is generated in situ. In such vaccines, the DNA may be present within any of a variety of delivery systems known to those of ordinary skill in the art, including nucleic acid expression systems, bacterial and viral expression systems. Appropriate nucleic acid expression systems contain the necessary DNA sequences for expression in the patient (such as a suitable promoter and terminator signal). Bacterial delivery systems involve the administration of a bacterium (such as Bacillus-Calmette-Guerrin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic, or defective, replication competent virus. Techniques for incorporating DNA into such expression systems are well known in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

A DNA vaccine as described above may be administered simultaneously with or sequentially to either a polypeptide of the present invention or a known mycobacterial antigen, such as the 38 kD antigen described above. For example, administration of DNA encoding a polypeptide of the present invention, may be followed by administration of an antigen in order to enhance the protective immune effect of the vaccine.

Routes and frequency of administration, as well as dosage, will vary from individual to individual and may parallel those currently being used in immunization using BCG. In general, the pharmaceutical compositions and vaccines may be administered by injection (e.g., intradermal, intramuscular, intravenous or subcutaneous), intranasally (e.g., by aspiration) or orally. Between 1 and 3 doses may be administered for a 1–36 week period. Preferably, 3 doses are administered, at intervals of 3–4 months, and booster vaccinations may be given periodically thereafter. Alternate protocols may be appropriate for individual patients. A suitable dose is an amount of polypeptide or DNA that, when administered as described above, is capable of raising an immune response in a patient sufficient to protect the patient from mycobacterial infection for at least 1–2 years. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 μg. Suitable dose sizes will vary with the size of the patient, but will typically range from about 0.1 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Any of a variety of adjuvants may be employed in the vaccines of this invention to non-specifically enhance the immune response. Most adjuvants contain a substance designed to protect the antigen from rapid catabolism, such as aluminum hydroxide or mineral oil, and a non-specific stimulator of immune responses, such as lipid A, *Bordetella pertussis, M. tuberculosis*, or, as discussed below, *M. vaccae*. Suitable adjuvants are commercially available as, for example, Freund's Incomplete Adjuvant and Freund's Complete Adjuvant (Difco Laboratories, Detroit, Mich.), and Merck Adjuvant 65 (Merck and Company, Inc., Rahway, N.J.). Other suitable adjuvants include alum, biodegradable microspheres, monophosphoryl lipid A and Quil A.

In another aspect, this invention provides methods for using one or more of the polypeptides described above to diagnose tuberculosis using a skin test. As used herein, a "skin test" is any assay performed directly on a patient in which a delayed-type hypersensitivity (DTH) reaction (such as swelling, reddening or dermatitis) is measured following intradermal injection of one or more polypeptides as described above. Preferably, the reaction is measured at least 48 hours after injection, more preferably 48–72 hours.

The DTH reaction is a cell-mediated immune response, which is greater in patients that have been exposed previously to the test antigen (i.e., the immunogenic portion of the polypeptide employed, or a variant thereof). The response may be measured visually, using a ruler. In general, a response that is greater than about 0.5 cm in diameter, preferably greater than about 1.0 cm in diameter, is a positive response, indicative of tuberculosis infection.

For use in a skin test, the polypeptides of the present invention are preferably formulated, as pharmaceutical compositions containing a polypeptide and a physiologically acceptable carrier, as described above. Such compositions typically contain one or more of the above polypeptides in an amount ranging from about 1 μg to about 100 μg, preferably from about 10 μg to about 50 μg in a volume of 0.1 mL. Preferably, the carrier employed in such pharmaceutical compositions is a saline solution with appropriate preservatives, such as phenol and/or Tween 8™.

In a preferred embodiment, a polypeptide employed in a skin test is of sufficient size such that it remains at the site of injection for the duration of the reaction period. In general, a polypeptide that is at least 9 amino acids in length is sufficient. The polypeptide is also preferably broken down by macrophages or dendritic cells within hours of injection to allow presentation to T-cells. Such polypeptides may contain repeats of one or more of the above sequences or other immunogenic or nonimmunogenic sequences.

In another aspect, methods are provided for detecting mycobacterial infection in a biological sample, using one or more of the above polypeptides, either alone or in combination. In embodiments in which multiple polypeptides are employed, polypeptides other than those specifically described herein, such as the 38 kD antigen described above, may be included. As used herein, a "biological sample" is any antibody-containing sample obtained from a patient. Preferably, the sample is whole blood, sputum, serum, plasma, saliva, cerebrospinal fluid or urine. More preferably, the sample is a blood, serum or plasma sample obtained from a patient or a blood supply. The polypeptide(s) are used in an assay, as described below, to determine the presence or absence of antibodies to the polypeptide(s) in the sample, relative to a predetermined cut-off value. The presence of such antibodies indicates the presence of mycobacterial infection.

In embodiments in which more than one polypeptide is employed, the polypeptides used are preferably complementary (i.e., one component polypeptide will tend to detect infection in samples where the infection would not be detected by another component polypeptide). Complementary polypeptides may generally be identified by using each polypeptide individually to evaluate serum samples obtained from a series of patients known to be infected with a Mycobacterium. After determining which samples test positive (as described below) with each polypeptide, combinations of two or more polypeptides may be formulated that are capable of detecting infection in most, or all, of the samples tested. For example, approximately 25–30% of sera from tuberculosis-infected individuals are negative for antibodies to any single protein, such as the 38 kD antigen mentioned above. Complementary polypeptides may, therefore, be used in combination with the 38 kD antigen to improve sensitivity of a diagnostic test.

A variety of assay formats employing one or more polypeptides to detect antibodies in a sample are well known in the art. See, e.g., Harlow and Lane, *Antibodies: A Laboratory Manual*, Cold Spring Harbor Laboratory, 1988. In a preferred embodiment, the assay involves the use of polypeptide immobilized on a solid support to bind to and remove the antibody from the sample. The bound antibody may then be detected using a detection reagent that contains a reporter group. Suitable detection reagents include antibodies that bind to the antibody/polypeptide complex and free polypeptide labelled with a reporter group (e.g., in a semi-competitive assay). Alternatively, a competitive assay may be utilized, in which an antibody that binds to the polypeptide is labelled with a reporter group and allowed to bind to the immobilized antigen after incubation of the antigen with the sample. The extent to which components of the sample inhibit the binding of the labelled antibody to the polypeptide is indicative of the reactivity of the sample with the immobilized polypeptide.

The solid support may be any solid material to which the antigen may be attached. Suitable materials are well known in the art. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptides may be bound to the solid support using a variety of techniques well known in the art. In the context of the present invention, the term "bound" refers to both noncovalent association, such as adsorption, and covalent attachment, which may be a direct linkage between the antigen and functional groups on the support or a linkage by way of a cross-linking agent. Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 µg, and preferably about 100 ng, is sufficient to bind an adequate amount of antigen.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook, 1991, at A12–A13).

In certain embodiments, the assay is an enzyme-linked immunosorbent assay (ELISA). This assay may be performed by first contacting a polypeptide antigen that has been immobilized on a solid support, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

More specifically, once the polypeptide is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.) may be employed. The immobilized polypeptide is then incubated with the sample, and antibody is allowed to bind to the antigen. The sample may be diluted with a suitable diluent, such as phosphate-buffered saline (PBS) prior to incubation. In general, an appropriate contact time, or incubation time, is that period of time that is sufficient to detect the presence of antibody within a *M. tuberculosis*-infected sample. Preferably, the contact time is sufficient to achieve a level of binding that is at least 95% of that achieved at equilibrium between bound and unbound antibody. The time necessary to achieve equilibrium may be readily determined by assaying the level of binding that occurs over a period of time. At room temperature, an incubation time of about 30 minutes is generally sufficient.

Unbound sample may be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known in the art. Common binding agents may also be purchased conjugated to a variety of reporter groups from many commercial sources (e.g., Zymed Laboratories, San Francisco, Calif., and Pierce, Rockford, Ill.).

The detection reagent is incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may be detected by the addition of substrate (generally for a specific period of time), followed by spectroscopic or other analysis of the reaction products.

To determine the presence or absence of anti-mycobacterial antibodies in the sample, the signal detected from the reporter group that remains bound to the solid support is generally compared to a signal that corresponds to a predetermined cut-off value. In one preferred embodiment, the cut-off value is the average mean signal obtained when the immobilized antigen is incubated with samples from an uninfected patient. In an alternate preferred embodiment, the cut-off value is determined using a Receiver Operator Curve, according to the method of Sackett et al., *Clinical Epidemiology: A Basic Sciencefor Clinical Medicine*, Little Brown and Co., 1985, pp. 106–107. In general, signals higher than the predetermined cut-off value are considered to be positive for mycobacterial infection.

The assay may also be performed in a rapid flow-through or strip test format, wherein the antigen is immobilized on a membrane, such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of anti-mycobacterial antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an ELISA, as discussed above. Preferably, the amount of polypeptide immobilized on the membrane ranges from about 25 ng to about 1 μg, and more preferably from about 50 ng to about 500 ng. Such tests can typically be performed with a very small amount (e.g., one drop) of patient serum or blood.

Numerous other assay protocols exist that are suitable for use with the polypeptides of the present invention. The above descriptions are intended to be exemplary only.

The present invention also provides antibodies to the inventive polypeptides. Antibodies may be prepared by any of a variety of techniques known to those of ordinary skill in the art. See, e.g., Harlow and Lane, *Antibodies: A Laboratory Manual*, Cold Spring Harbor Laboratory, 1988. In one such technique, an immunogen comprising the antigenic polypeptide is initially injected into any of a wide variety of mammals (e.g., mice, rats, rabbits, sheep and goats). The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells may then be immortalized by fusion with a myeloma cell fusion partner, preferably one that is syngeneic with the immunized animal, using one of a variety of techniques well known in the art.

Monoclonal antibodies may be isolated from the supernatants of the resulting hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood.

Antibodies may be used in diagnostic tests to detect the presence of mycobacterial antigens using assays similar to those detailed above and other techniques well known to those of skill in the art, thereby providing a method for detecting mycobacterial infection, such as *M. tuberculosis* infection, in a patient.

Diagnostic reagents of the present invention may also comprise DNA sequences encoding one or more of the above polypeptides, or one or more portions thereof. For example, primers comprising at least 10 contiguous oligonucleotides of the subject DNA sequences may be used in polymerase chain reaction (PCR) based tests. Similarly, probes comprising at least 18 contiguous oligonucleotides of the subject DNA sequences may be used for hybridizing to specific sequences. Techniques for both PCR based tests and hybridization tests are well known in the art. Primers or probes may thus be used to detect *M. tuberculosis* and other mycobacterial infections in biological samples, preferably sputum, blood, serum, saliva, cerebrospinal fluid or urine. DNA probes or primers comprising oligonucleotide sequences described above may be used alone, in combination with each other, or with previously identified sequences, such as the 38 kD antigen discussed above.

As discussed above, effective vaccines contain at least two different components. The first is a polypeptide comprising an antigen, which is processed by macrophages and other antigen-presenting cells and displayed for $CD4^+$ T cells or for $CD8^+$ T cells. This antigen forms the "specific" target of an immune response. The second component of a vaccine is a non-specific immune response amplifier, such as an adjuvant or a liposome, into which the antigen is incorporated. An adjuvant amplifies immune responses to a structurally unrelated compound or polypeptide. Several adjuvants are prepared from microbes such as *Bordetella pertussis*, *M. tuberculosis* and *M. bovis* BCG. Adjuvants may also contain components designed to protect polypeptide antigens from degradation, such as aluminum hydroxide or mineral oil.

While the antigenic component of a vaccine contains polypeptides that direct the immune attack against a specific pathogen, such as *M. tuberculosis*, the adjuvant is often capable of broad use in many different vaccine formulations. Certain pathogens, such as *M. tuberculosis*, as well as certain cancers, are effectively contained by an immune attack directed by T cells, $CD4^+$ T cells or $CD8^+$ T cells, known as cell-mediated immunity. Other pathogens, such as poliovirus, also require antibodies produced by B cells for containment. These different classes of immune attack (T cell or B cell) are controlled by different subpopulations of $CD4^+$ T cells, commonly referred to as Th1 and Th2 cells. A desirable property of an adjuvant is the ability to selectively amplify the function of either Th1 or Th2 populations of $CD4^+$ T cells.

As shown below in Example 5, *M. vaccae* and a modified (delipidated) form of autoclaved *M. vaccae* have been found to have adjuvant properties. Furthermore, it has been found that *M. vaccae* produces compounds which amplify the immune response to *M. vaccae* antigens, as well as to antigens from other sources. The present invention thus provides methods for enhancing immune responses to an antigen comprising administering killed *M. vaccae* cells, *M. vaccae* culture filtrate or delipidated *M. vaccae* cells.

The following examples are offered by way of illustration and not by way of limitation.

EXAMPLE 1

EFFECT OF IMMUNIZATION OF MICE WITH *M. vaccae* ON TUBERCULOSIS

This example illustrates the effect of immunization with *M. vaccae* or *M. vaccae* culture filtrate in mice prior to challenge with live *M. tuberculosis*.

*M. vaccae* (ATCC Number 15483) was cultured in sterile Medium 90 (yeast extract, 2.5 g/l; tryptone, 5 g/l; glucose, 1 g/l) at 37° C. The cells were harvested by centrifugation, and transferred into sterile Middlebrook 7H9 medium (Difco Laboratories, Detroit, Mich., USA) with glucose at 37° C. for one day. The medium was then centrifuged to pellet the bacteria, and the culture filtrate removed. The bacterial pellet was resuspended in phosphate buffered saline at a concentration of 10 mg/ml, equivalent to $10^{10}$ *M. vaccae* organisms per ml. The cell suspension was then autoclaved for 15 min at 120° C. The culture filtrate was passaged through a 0.45 μM filter into sterile bottles.

As shown in FIG. 1A, when mice were immunized with 1 mg, 100 μg or 10 μg of *M. vaccae* and infected three weeks later with 5×10⁵ colony forming units (CFU) of live *M. tuberculosis* H37Rv, significant protection from infection was seen. In this example, spleen, liver and lung tissue was harvested from mice three weeks after infection, and live bacilli determined (expressed as CFU). The reduction in bacilli numbers, when compared to tissue from non-immunized control mice, exceeded 2 logs in liver and lung tissue, and 1 log in spleen tissue. Immunization of mice with heat-killed *M. tuberculosis* H37Rv had no significant protective effects on mice subsequently infected with live *M. tuberculosis* H37Rv.

Figure 1B:
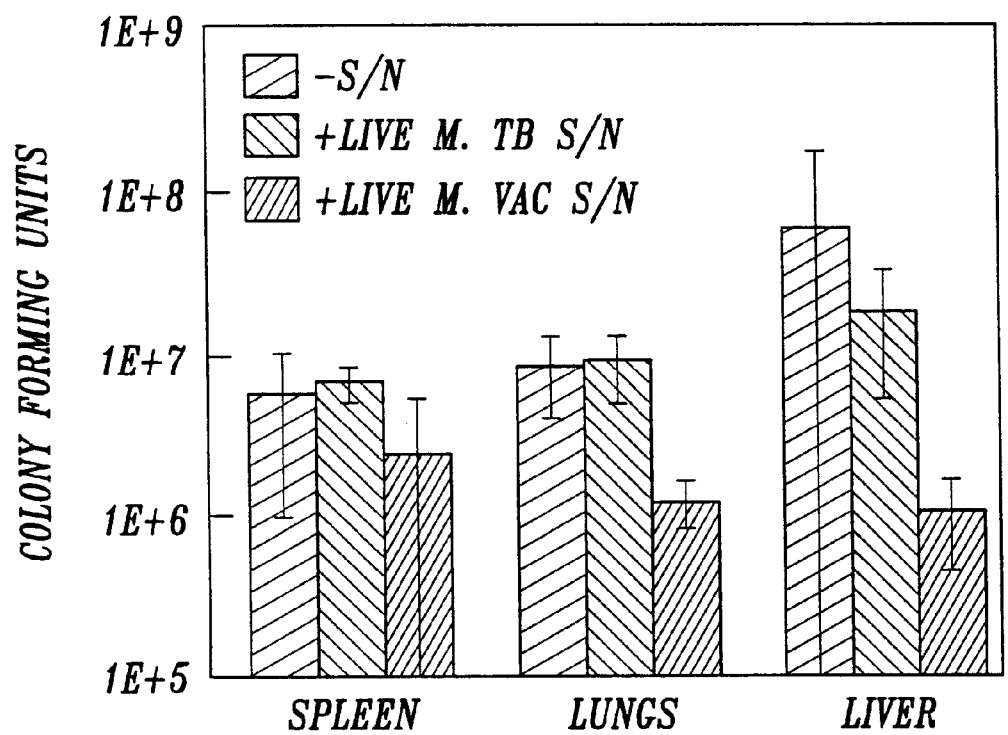
Figure 2A:
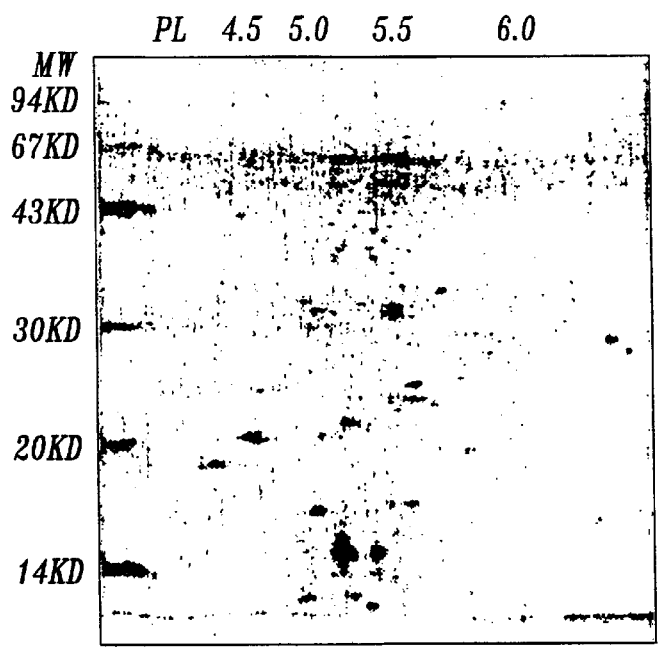
FIGS. 2A and B show components of M. vaccae and M. tuberculosis culture filtrates, respectively, as analyzed by 2-dimensional polyacrylamide gel electrophoresis.
Figure 2B:
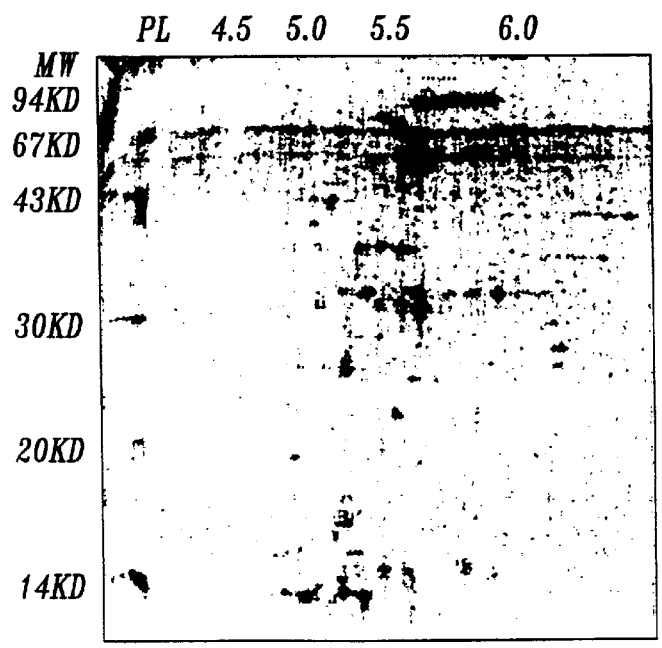

FIG. 1B shows that when mice were immunized with 100 μg of *M. vaccae* culture filtrate, and infected three weeks later with 5×10⁵ CFU of *M. tuberculosis* H37Rv, significant protection was also seen. When spleen, liver and lung tissue was harvested from mice three weeks after infection, and live bacilli numbers (CFU) determined, a 1–2 log reduction in numbers, as compared to non-immunized control mice, was observed.

EXAMPLE 2

PURIFICATION AND CHARACTERIZATION OF POLYPEPTIDES FROM *M. vaccae* CULTURE FILTRATE This example illustrates the preparation of *M. vaccae* soluble proteins from culture filtrate. Unless otherwise noted, all percentages in the following example are weight per volume.

*M. vaccae* (ATCC Number 15483) was cultured in sterile Medium 90 at 37° C. The cells were harvested by centrifugation, and transferred into sterile Middlebrook 7H9 medium with glucose at 37° C. for one day. The medium was then centrifuged (leaving the bulk of the cells) and filtered through a 0.45μ filter into sterile bottles.

The culture filtrate was concentrated by lyophilization, and redissolved in MilliQ water. A small amount of insoluble material was removed by filtration through a 0.45μ membrane. The culture filtrate was desalted by membrane filtration in a 400 ml Amicon stirred cell which contained a 3,000 kilodalton molecular weight cut-off (MWCO) membrane. The pressure was maintained at 50 psi using nitrogen gas. The culture filtrate was repeatedly concentrated by membrane filtration and diluted with water until the conductivity of the sample was less than 1.0 mS. This procedure reduced the 20l volume to approximately 50 ml. Protein concentrations were determined by the Bradford protein assay (Bio-Rad, Hercules, Calif., USA).

The desalted culture filtrate was fractionated by ion exchange chromatography on a column of Q-Sepharose (Pharmacia Biotech, Uppsala, Sweden) (16×100 mm) equilibrated with 10 mM Tris HCl buffer pH 8.0. Polypeptides were eluted with a linear gradient of NaCl from 0 to 1.0 M in the above buffer system. The column eluent was monitored at a wavelength of 280 nm.

The pool of polypeptides eluting from the ion exchange column was concentrated in a 400 ml Amicon stirred cell which contained a 3,000 MWCO membrane. The pressure was maintained at 50 psi using nitrogen gas. The polypeptides were repeatedly concentrated by membrane filtration and diluted with 1% glycine until the conductivity of the sample was less than 0.1 mS.

The purified polypeptides were then fractionated by preparative isoelectric focusing in a Rotofor device (Bio-Rad, Hercules, Calif., USA). The pH gradient was established with a mixture of Ampholytes (Pharmacia Biotech) comprising 1.6% pH 3.5–5.0 Ampholytes and 0.4% pH 5.0–7.0 Ampholytes. Acetic acid (0.5 M) was used as the anolyte, and 0.5 M ethanolamine as the catholyte. Isoelectric focusing was carried out at 12W constant power for 6 hours, following the manufacturer's instructions. Twenty fractions were obtained.

Fractions from isoelectric focusing were combined, and the polypeptides were purified on a Vydac C4 column (Separations Group, Hesperia, Calif., USA) 300 Angstrom pore size, 5 micron particle size (10×250 mm). The polypeptides were eluted from the column with a linear gradient of acetonitrile (0–80% v/v) in 0.05% (v/v) trifluoroacetic acid (TFA). The flow-rate was 2.0 ml/min and the HPLC eluent was monitored at 220 nm. Fractions containing polypeptides were collected to maximize the purity of the individual samples.

Relatively abundant polypeptide fractions were rechromatographed on a Vydac C4 column (Separations Group) 300 Angstrom pore size, 5 micron particle size (4.6×250 mm). The polypeptides were eluted from the column with a linear gradient from 20–60% (v/v) of acetonitrile in 0.05% (v/v) TFA at a flow-rate of 1.0 ml/min. The column eluent was monitored at 220 nm. Fractions containing the eluted polypeptides were collected to maximise the purity of the individual samples. Approximately 20 polypeptide samples were obtained and they were analyzed for purity on a polyacrylamide gel according to the procedure of Laemmli (Laemmli, U. K., *Nature* 277:680–685, 1970).

The polypeptide fractions which were shown to contain significant contamination were further purified using a Mono Q column (Pharmacia Biotech) 10 micron particle size (5×50 mm) or a Vydac Diphenyl column (Separations Group) 300 Angstrom pore size, 5 micron particle size (4.6×250 mm). From a Mono Q column, polypeptides were eluted with a linear gradient from 0–0.5 M NaCl in 10 mM Tris HCl pH 8.0. From a Vydac Diphenyl column, polypeptides were eluted with a linear gradient of acetonitrile (20–60% v/v) in 0.1% TFA. The flow-rate was 1.0 ml/min and the column eluent was monitored at 220 nm for both columns. The polypeptide peak fractions were collected and analyzed for purity on a 15% polyacrylamide gel as described above.

For sequencing, the polypeptides were individually dried onto Biobrene™ (Perkin Elmer/Applied BioSystems Division, Foster City, Calif.)-treated glass fiber filters. The filters with polypeptide were loaded onto a Perkin Elmer/Applied BioSystems Procise 492 protein sequencer and the polypeptides were sequenced from the amino terminal end using traditional Edman chemistry. The amino acid sequence was determined for each polypeptide by comparing the retention time of the PTH amino acid derivative to the appropriate PTH derivative standards.

Internal sequences were also determined on some antigens by digesting the antigen with the endoprotease Lys-C, or by chemically cleaving the antigen with cyanogen bromide. Peptides resulting from either of these procedures were separated by reversed-phase HPLC on a Vydac C18 column using a mobile phase of 0.05% (v/v) trifluoroacetic acid with a gradient of acetonitrile containing 0.05% (v/v) TFA (1%/min). The eluent was monitored at 214 nm. Major internal peptides were identified by their UV absorbance, and their N-terminal sequences were determined as described above.

Using the procedures described above, five soluble *M. vaccae* antigens, designated GVc-1, GVc-2, GVc-7, GVc-13 and GVc-20, were isolated. Determined N-terminal and internal sequences for GVc-1 are shown in SEQ ID NOS: 1, 2 and 3, respectively; the N-terminal sequence for GVc-2 is shown in SEQ ID NO: 4; internal sequences for GVc-7 are shown in SEQ ID NOS: 5–8; internal sequences for GVc-13 are shown in SEQ ID NOS: 9–11; and internal sequence for GVc-20 is shown in SEQ ID NO: 12. Each of the internal peptide sequences provided herein begins with an amino acid residue which is assumed to exist in this position in the polypeptide, based on the known cleavage specificity of cyanogen bromide (Met) or Lys-C (Lys).

Three additional polypeptides, designated GVc-16, GVc-18 and GVc-21, were isolated employing a preparative sodium dodecyl sulfate-polyacrylamide gel electrophoresis (SDS-PAGE) purification step in addition to the preparative isoelectric focusing procedure described above. Specifically, fractions comprising mixtures of polypeptides from the preparative isoelectric focusing purification step previously described, were purified by preparative SDS-PAGE on a 15% polyacrylamide gel. The samples were dissolved in reducing sample buffer and applied to the gel. The separated proteins were transferred to a polyvinylidene difluoride (PVDF) membrane by electroblotting in 10 mM 3-(cyclohexylamino)-1-propanesulfonic acid (CAPS) buffer pH 11 containing 10% (v/v) methanol. The transferred protein bands were identified by staining the PVDF membrane with Coomassie blue. Regions of the PVDF membrane containing the most abundant polypeptide species were cut out and directly introduced into the sample cartridge of the Perkin Elmer/Applied BioSystems Procise 492 protein sequencer. Protein sequences were determined as described above. The N-terminal sequences for GVc-16, GVc-18 and GVc-21 are provided in SEQ ID NOS: 13, 14 and 15, respectively.

Additional antigens, designated GVc-12, GVc-14, GVc-15, GVc-17 and GVc-19, were isolated employing a preparative SDS-PAGE purification step in addition to the chromatographic procedures described above. Specifically, fractions comprising a mixture of antigens from the Vydac C4 HPLC purification step previously described were fractionated by preparative SDS-PAGE on a polyacrylamide gel. The samples were dissolved in non-reducing sample buffer and applied to the gel. The separated proteins were transferred to a PVDF membrane by electroblotting in 10 mM CAPS buffer, pH 11 containing 10% (v/v) methanol. The transferred protein bands were identified by staining the PVDF membrane with Commassie blue. Regions of the PVDF membrane containing the most abundant polypeptide species were cut out and directly introduced into the sample cartridge of the Perkin Elmer/Applied BioSystems Procise 492 protein sequencer. Protein sequences were determined as described above. The determined N-terminal sequences for GVc-12, GVc-14, GVc-15, GVc-17 and GVc-19 are provided in SEQ ID NOS: 16–20, respectively.

All of the above amino acid sequences were compared to known amino acid sequences in the SwissProt data base (version R32) using the GeneAssist system. No significant homologies to the amino acid sequences GVc-2 to GVc-21 were obtained. The amino acid sequence for GVc-1 was found to bear some similarity to sequences previously identified from M. bovis and M. tuberculosis.

The purified polypeptides were screened for the ability to induce T-cell proliferation and IFN-γ in peripheral blood cells from immune human donors. These donors were known to be PPD (purified protein derivative from *M. tuberculosis*) skin test positive and their T cells were shown to proliferate in response to PPD. Donor PBMCs and crude soluble proteins from *M. vaccae* culture filtrate were cultured in medium comprising RPMI 1640 supplemented with 10% (v/v) autologous serum, penicillin (60 μg/ml), streptomycin (100 μg/ml), and glutamine (2 mM).

After 3 days, 50 μl of medium was removed from each well for the determination of IFN-γ levels, as described below. The plates were cultured for a further 4 days and then pulsed with 1 μCi/well of tritiated thymidine for a further 18 hours, harvested and tritium uptake determined using a scintillation counter. Fractions that stimulated proliferation in both replicates two-fold greater than the proliferation observed in cells cultured in medium alone were considered positive.

IFN-γ was measured using an enzyme-linked immunosorbent assay (ELISA). ELISA plates were coated with a mouse monoclonal antibody directed to human IFN-γ (Endogen, Wobural, Mass.) 1 μg/ml phosphate-buffered saline (PBS) for 4 hours at 4° C. Wells were blocked with PBS containing 0.2% Tween 20 for 1 hour at room temperature. The plates were then washed four times in PBS/0.2% Tween 20, and samples diluted 1:2 in culture medium in the ELISA plates were incubated overnight at room temperature. The plates were again washed, and a biotinylated polyclonal rabbit anti-human IFN-γ serum (Endogen), diluted to 1 μg/ml in PBS, was added to each well. The plates were then incubated for 1 hour at room temperature, washed, and horseradish peroxidase-coupled avidin A (Vector Laboratories, Burlingame, Calif.) was added at a 1:4,000 dilution in PBS. After a further 1 hour incubation at room temperature, the plates were washed and orthophenylenediamine (OPD) substrate added. The reaction was stopped after 10 min with 10% (v/v) HCl. The optical density (OD) was determined at 490 nm. Fractions that resulted in both replicates giving an OD two-fold greater than the mean OD from cells cultured in medium alone were considered positive.

Examples of polypeptides containing sequences that stimulate peripheral blood mononuclear cells (PBMC) T cells to proliferate and produce IFN-γ are shown in Table 1, wherein (−) indicates a lack of activity, (+/−) indicates polypeptides having a result less than twice higher than background activity of control media, (+) indicates polypeptides having activity two to four times above background, and (++) indicates polypeptides having activity greater than eight times above background.

TABLE 1

| Antigen | Proliferation | IFN-γ |
|---|---|---|
| GVc-1 | ++ | +/− |
| GVc-2 | + | ++ |
| GVc-7 | +/− | − |
| GVc-13 | + | ++ |
| GVc-14 | ++ | + |
| GVc-15 | + | + |
| GVc-20 | + | + |

EXAMPLE 3

PURIFICATION AND CHARACTERIZATION OF POLYPEPTIDES FROM *M. vaccae* CULTURE FILTRATE BY 2-DIMENSIONAL POLYACRYLAMIDE GEL ELECTROPHORESIS

*M. vaccae* soluble proteins were isolated from culture filtrate using 2-dimensional polyacrylamide gel electrophoresis as described below. Unless otherwise noted, all percentages in the following example are weight per volume.

M. vaccae (ATCC Number 15483) was cultured in sterile Medium 90 at 37° C. M. tuberculosis strain H37Rv (ATCC number 27294) was cultured in sterile Middlebrook 7H9 medium with Tween 80 and oleic acid/albumin/dextrose/catalase additive (Difco Laboratories, Detroit, Mich.). The cells were harvested by centrifugation, and transferred into sterile Middlebrook 7H9 medium with glucose at 37° C. for one day. The medium was then centrifuged (leaving the bulk of the cells) and filtered through a 0.45μ filter into sterile bottles. The culture filtrate was concentrated by lyophilisation, and redissolved in MilliQ water. A small amount of insoluble material was removed by filtration through a 0.45$\mu$ membrane filter.

The culture filtrate was desalted by membrane filtration in a 400 ml Amicon stirred cell which contained a 3,000 MWCO membrane. The pressure was maintained at 60 psi using nitrogen gas. The culture filtrate was repeatedly concentrated by membrane filtration and diluted with water until the conductivity of the sample was less than 1.0 mS. This procedure reduced the 20 L volume to approximately 50 mL. Protein concentrations were determined by the Bradford protein assay (Bio-Rad, Hercules, Calif., USA).

The desalted culture filtrate was fractionated by ion exchange chromatography on a column of Q-Sepharose (Pharmacia Biotech) (16×100 mm) equilibrated with 10 mM TrisHCL buffer pH 8.0. Polypeptides were eluted with a linear gradient of NaCl from 0 to 1.0 M in the above buffer system. The column eluent was monitored at a wavelength of 280 nm.

The pool of polypeptides eluting from the ion exchange column were fractionated by preparative 2D gel electrophoresis. Samples containing 200–500 ug of polypeptide were made 8M in urea and applied to polyacrylamide isoelectric focusing rod gels (diameter 2mm, length 150 mm, pH 5–7). After the isoelectric focusing step, the first dimension gels were equilibrated with reducing buffer and applied to second dimension gels (16% polyacrylamide). FIGS. 2A and 2B are the 2-D gel patterns observed with *M. vaccae* culture filtrate and *M. tuberculosis* H37Rv culture filtrate, respectively. Polypeptides from the second dimension separation were transferred to PVDF membranes by electroblotting in 10 mM CAPS buffer pH 11 containing 10% (v/v) methanol. The PVDF membranes were stained for protein with Coomassie blue. Regions of PVDF containing polypeptides of interest were cut out and directly introduced into the sample cartridge of the Perkin Elmer/Applied Bio-Systems Procise 492 protein sequencer. The polypeptides were sequenced from the amino terminal end using traditional Edman chemistry. The amino acid sequence was determined for each polypeptide by comparing the retention time of the PTH amino acid derivative to the appropriate PTH derivative standards. Using these procedures, nine polypeptides, designated GVs-1, GVs-3, GVs-4, GVs-5, GVs-6, GVs-8, GVs-9, GVs-10 and GVs-11, were isolated. The determined N-terminal sequences for these polypeptides are shown in SEQ ID NOS: 21–29, respectively.

All of these amino acid sequences were compared to known amino acid sequences in the SwissProt data base (version R32) using the GeneAssist system. No significant homologies were obtained, with the exceptions of GVs-3, GVs-4 and GVs-5. These three sequences were found to bear some similarity to the antigen 85A and 85B proteins from *M. leprae* (SEQ ID NOS: 30 and 31, respectively), *M. tuberculosis* (SEQ ID NOS: 32 and 33, respectively) and *M. bovis* (SEQ ID NOS: 34 and 35, respectively), and the antigen 85C proteins from *M. leprae* (SEQ ID NO: 36) and *M. tuberculosis* (SEQ ID NO: 37). A comparison of the inventive antigen 85A protein from *M. vaccae* with those from *M. tuberculosis, M. bovis* and *M. leprae*, is presented in FIG. 3.

EXAMPLE 4

DNA CLONING STRATEGY FOR THE *M. vaccae* ANTIGEN 85 SERIES

Probes for antigens 85A, 85B, and 85C (SEQ ID NOS: 38 and 39) were prepared by the polymerase chain reaction (PCR) using degenerate oligonucleotides designed to regions of antigen 85 genomic sequence that are conserved between family members in a given mycobacterial species, and between mycobacterial species. These oligonucleotides were used under reduced stringency conditions to amplify target sequences from *M. vaccae* genomic DNA. An appropriately-sized 0.5 kb band was identified, purified, and cloned into T-tailed p Bluescript II SK (Stratagene, La Jolla, Calif.). Twenty-four individual colonies were screened at random for the presence of the antigen 85 PCR product, then sequenced using the Perkin Elmer/Applied Biosystems Model 377 automated sequencer and the M13-based primers, T3 and T7. Homology searches of the GenBank databases showed that twenty-three clones contained insert with significant homology to published antigen 85 genes from *M. tuberculosis* and *M. bovis*. Approximately half were most homologous to antigen 85C gene sequences, with the remainder being more similar to antigen 85B sequences. In addition, these two putative *M. vaccae* antigen 85 genomic sequences were 80% homologous to one another. Because of this high similarity, the antigen 85C PCR fragment was chosen to screen *M. vaccae* genomic libraries at low stringency for all three antigen 85 genes.

An *M. vaccae* genomic library was created in λ ZapExpress (Stratagene, La Jolla, Calif.) by cloning BamHI partially-digested *M. vaccae* genomic DNA into similarly-digested λ vector, with $3.4 \times 10^5$ independent plaque-forming units resulting. For screening purposes, twenty-seven thousand plaques from this non-amplified library were plated at low density onto eight 100 $cm^2$ plates. For each plate, duplicate plaque lifts were taken onto Hybond-$N^+$ nylon membrane (Amersham International, United Kingdom), and hybridized under reduced-stringency conditions (55° C.) to the radiolabelled antigen 85C PCR product. Autoradiography demonstrated that seventy-nine plaques consistently hybridised to the antigen 85C probe under these conditions. Thirteen positively-hybridising plaques were selected at random for further analysis and removed from the library plates, with each positive clone being used to generate secondary screening plates containing about two hundred plaques. Duplicate lifts of each plate were taken using Hybond-$N^+$ nylon membrane, and hybridised under the conditions used in primary screening. Multiple positively-hybridising plaques were identified on each of the thirteen plates screened. Two well-isolated positive phage from each secondary plate were picked for further analysis. Using in vitro excision, twenty-six plaques were converted into phagemid, and restriction-mapped. It was possible to group clones into four classes on the basis of this mapping. Sequence data from the 5' and 3' ends of inserts from several representatives of each group was obtained using the Applied Biosystems Model 377 automated sequencer and the T3 and T7 primers. Sequence homologies were determined using FASTA analysis of the GenBank databases with the GeneAssist software package. Two of these sets of clones were found to be homologous to *M. bovis* and *M. tuberculosis* antigen 85A genes, each containing either the 5' or 3' ends of the *M. vaccae* gene (this gene was cleaved during library construction as it contains an internal BamHI site). The remaining clones were found to contain sequences homologous to antigens 85B and 85C from a number of mycobacterial species. To determine the remaining nucleotide sequence for each gene, appropriate subclones were constructed and sequenced. Overlapping sequences were aligned using the DNA Strider software. The determined DNA sequences for *M. vaccae* antigens 85A, 85B and 85C are shown in SEQ ID NOS: 40–42, respectively, with the predicted amino acid sequences being shown in SEQ ID NOS: 43–45, respectively.

EXAMPLE 5

DNA CLONING STRATEGY FOR *M. vaccae* ANTIGENS

An 84 bp probe for the *M. vaccae* antigen GVc-7 was amplified using degenerate oligonucleotides designed to the determined amino acid sequence of GVc-7 (SEQ ID NOS: 5–8). This probe was used to screen a *M. vaccae* genomic DNA library as described in Example 4. The determined nucleotide sequence for GVc-7 is shown in SEQ ID NO: 46 and predicted amino acid sequence in SEQ ID NO: 47. Comparison of this sequence with known sequences in the gene bank as described above revealed no known homologies.

A redundant oligonucleotide probe was designed to the GVs-8 peptide sequence shown in SEQ ID NO: 26 and used to screen an *M. vaccae* genomic DNA library as described above. Positive plaques were isolated.

Four different genomic clones were identified, hereinafter referred to as GVs-8A, GVs-8B and GVs-8C and GVs-8D. The determined DNA sequences for the clones GVs-8A, GVs-8B, GVs-8C and GVs-8D are shown in SEQ ID NOS: 48–51, respectively, with the corresponding amino acid sequences being shown in SEQ ID NOS: 52–55, respectively. The clone GVs-8A contains regions showing some similarity to known prokaryotic valyl-tRNA synthetases; GVs-8B shows some similarity to *M. smegmatis* semialdehyde dehydrogenase; and GVs-8C shows some similarity to the *H. influenzea* folypolyglutamate synthase gene. GVs-8D contains an open reading frame which shows some similarity to sequences previously identified in *M. tuberculosis* and *M. leprae*, but whose function has not been identified.

EXAMPLE 6

DETECTION OF NONSPECIFIC IMMUNE AMPLIFIER FROM WHOLE *M. vaccae* AND THE CULTURE FILTRATE OF *M. vaccae*

This example illustrates the preparation of whole *M. vaccae* and *M. vaccae* culture filtrate and its non-specific immune amplifying or 'adjuvant' property.

*M. vaccae* bacteria was cultured, pelleted and autoclaved as described in Example 1. Culture filtrates of live *M. vaccae* refer to the supernatant from 24 hour cultures of *M. vaccae* in 7H9 medium with glucose. A delipidated form of *M. vaccae* was prepared by sonicating autoclaved *M. vaccae* for four bursts of 30 seconds on ice using the Virsonic sonicator (Virtis, Disa, USA). The material was then centrifuged (9000 rpm, 20 minutes, JA10 rotor, brake=5). The resulting pellet was suspended in 100 ml of chloroform/methanol (2:1), incubated at room temperature for 1 hour; recentrifuged, and the chloroform/methanol extraction repeated. The pellet was obtained by centrifugation, dried in vacuo, weighed and resuspended in PBS at 50 mg (dry weight) per ml as delipidated *M. vaccae*.

Glycolipids were removed from the delipidated *M. vaccae* preparation by refluxing in 50% v/v ethanol for 2 hours. The insoluble material was collected by centrifugation (10,000 rpm, JA20 rotor, 15 mins, brake=5). The extraction with 50% v/v ethanol under reflux was repeated twice more. The insoluble material was collected by centrifugation and washed in PBS. Proteins were extracted by resuspending the pellet in 2% SDS in PBS at 56° C. for 2 hours. The insoluble material was collected by centrifugation and the extraction with 2% SDS/PBS at 56° C. was repeated twice more. The pooled SDS extracts were cooled to 4° C., and precipitated SDS was removed by centrifugation (10,000 rpm, JA20 rotor, 15 mins, brake=5). Proteins were precipitated from the supernatant by adding an equal volume of acetone and incubating at −20° C. for 2 hours. The precipitated proteins were collected by centrifugation, washed in 50% v/v acetone, dried in vacuo, and redissolved in PBS.

*M. vaccae* culture supernatant (S/N), killed *M. vaccae* and delipidated *M. vaccae* were tested for adjuvant activity in the generation of cytotoxic T cell immune response to ovalbumin, a structurally unrelated protein, in the mouse. This anti-ovalbumin-specific cytotoxic response was detected as follows. C57BL/6 mice (2 per group) were immunized by the intraperitoneal injection of 100 μg of ovalbumin with the following test adjuvants: autoclaved *M. vaccae*; delipidated *M. vaccae*; delipidated *M. vaccae* with glycolipids also extracted and proteins extracted with SDS; the SDS protein extract treated with pronase (an enzyme which degrades protein); whole *M. vaccae* culture filtrate; and heat-killed *M. tuberculosis* or heat-killed *M. bovis* BCG, *M. phlei* or *M. smegmatus* or *M. vaccae* culture filtrate. After 10 days, spleen cells were stimulated in vitro for a further 6 days with E.G7 cells which are EL4 cells (a C57BL/6-derived T cell lymphoma) transfected with the ovalbumin gene and thus express ovalbumin. The spleen cells were then assayed for their ability to kill non-specifically EL4 target cells or to kill specifically the E.G7 ovalbumin expressing cells. Killing activity was detected by the release of $^{51}$Chromium with which the EL4 and E.G7 cells have been labelled (100 μCi per $2 \times 10^6$), prior to the killing assay. Killing or cytolytic activity is expressed as % specific lysis using the formula:

$$\frac{\text{cpm in test cultures} - \text{cpm in control cultures}}{\text{total cpm} - \text{cpm in control cultures}} \times 100\%$$

It is generally known that ovalbumin-specific cytotoxic cells are generated only in mice immunized with ovalbumin with an adjuvant but not in mice immunized with ovalbumin alone.

Figure 4A:
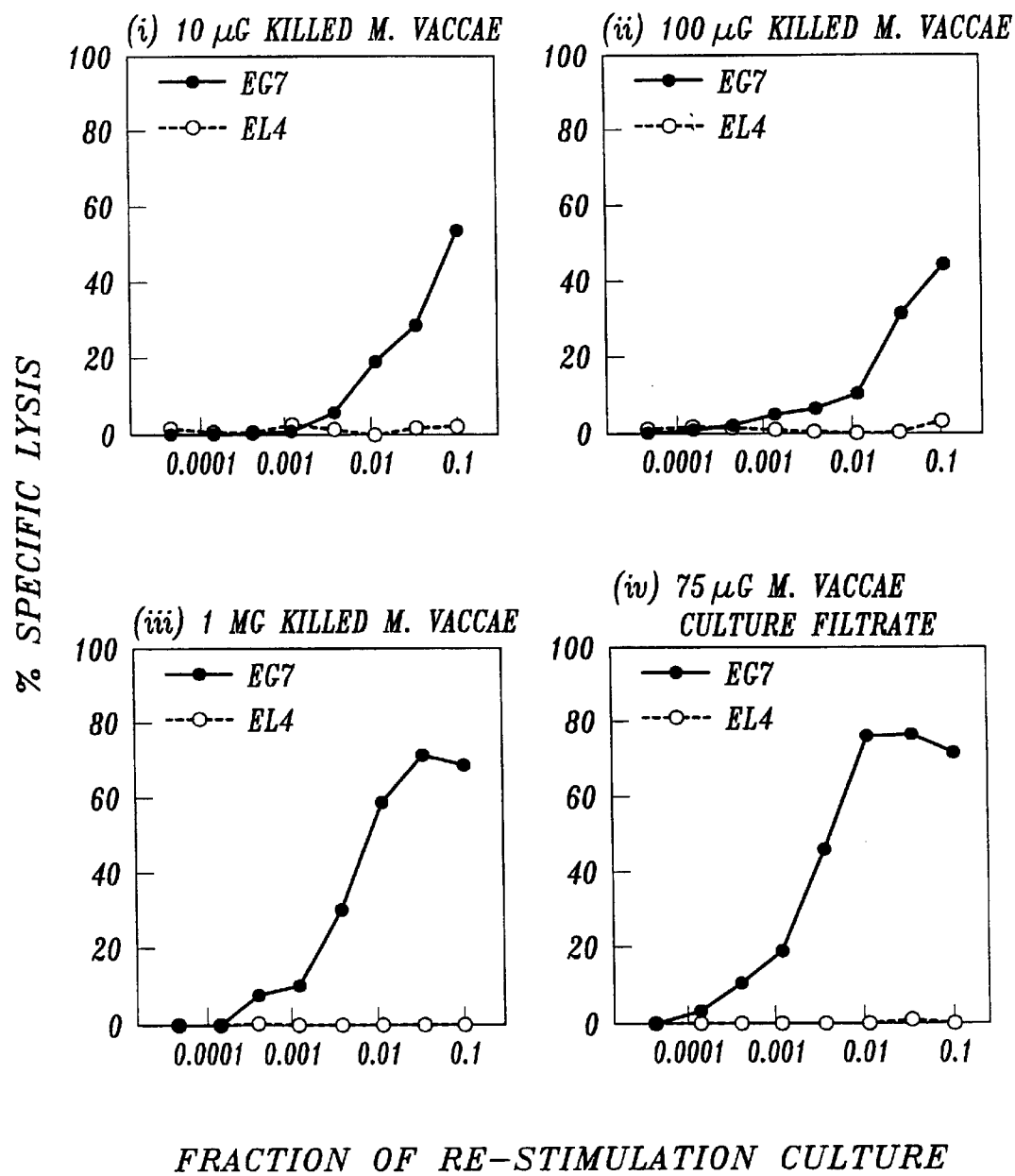
FIGS. 4A(i)–(iv) illustrate the non-specific immune amplifying effects of 10 μg, 100 μg and 1 mg autoclaved M. vaccae and 75 μg unfractionated culture filtrates of M. vaccae, respectively.
Figure 4B:
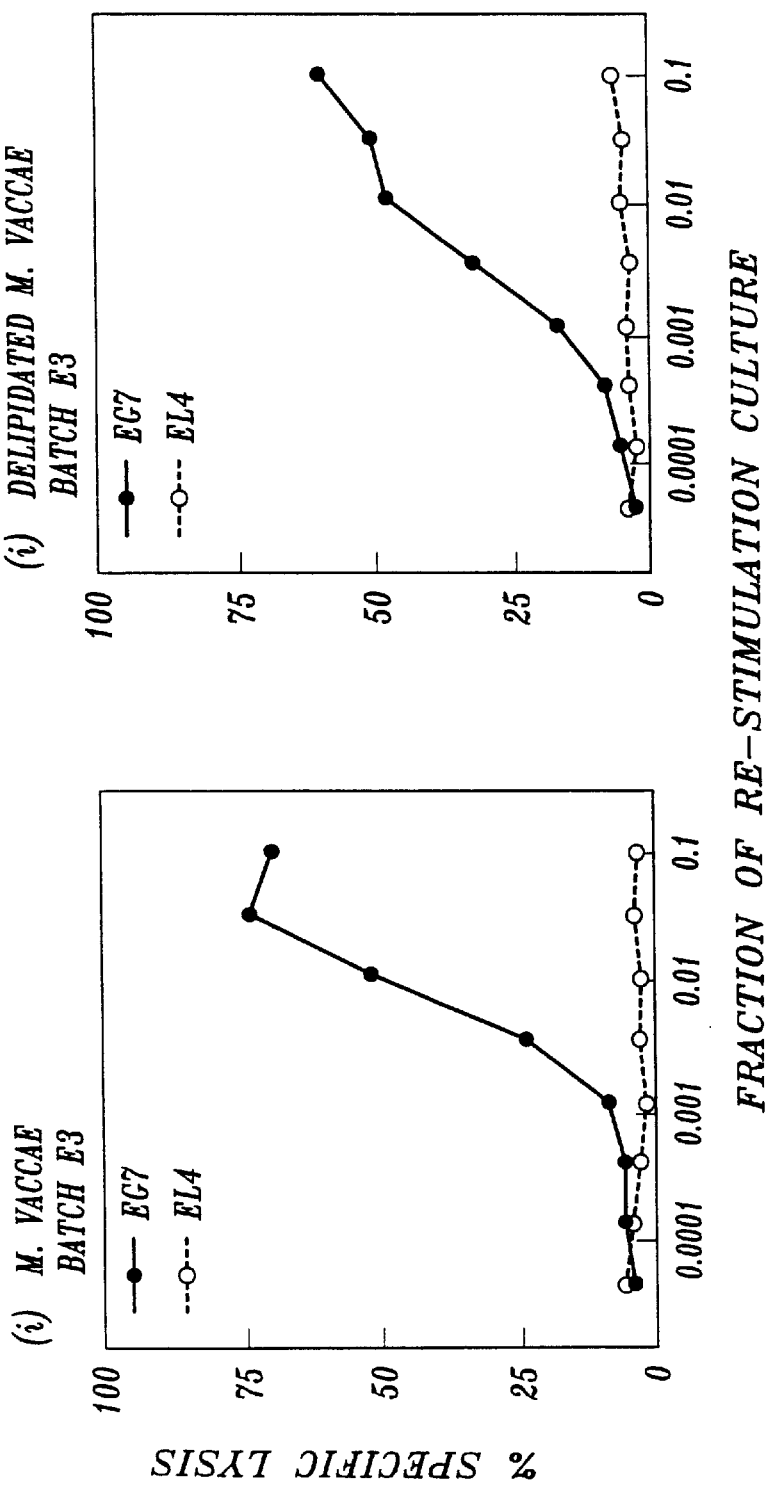
FIGS. 4B(i) and (ii) illustrate the non-specific immune amplifying effects of autoclaved M. vaccae and delipidated M. vaccae, respectively.
Figure 4C:
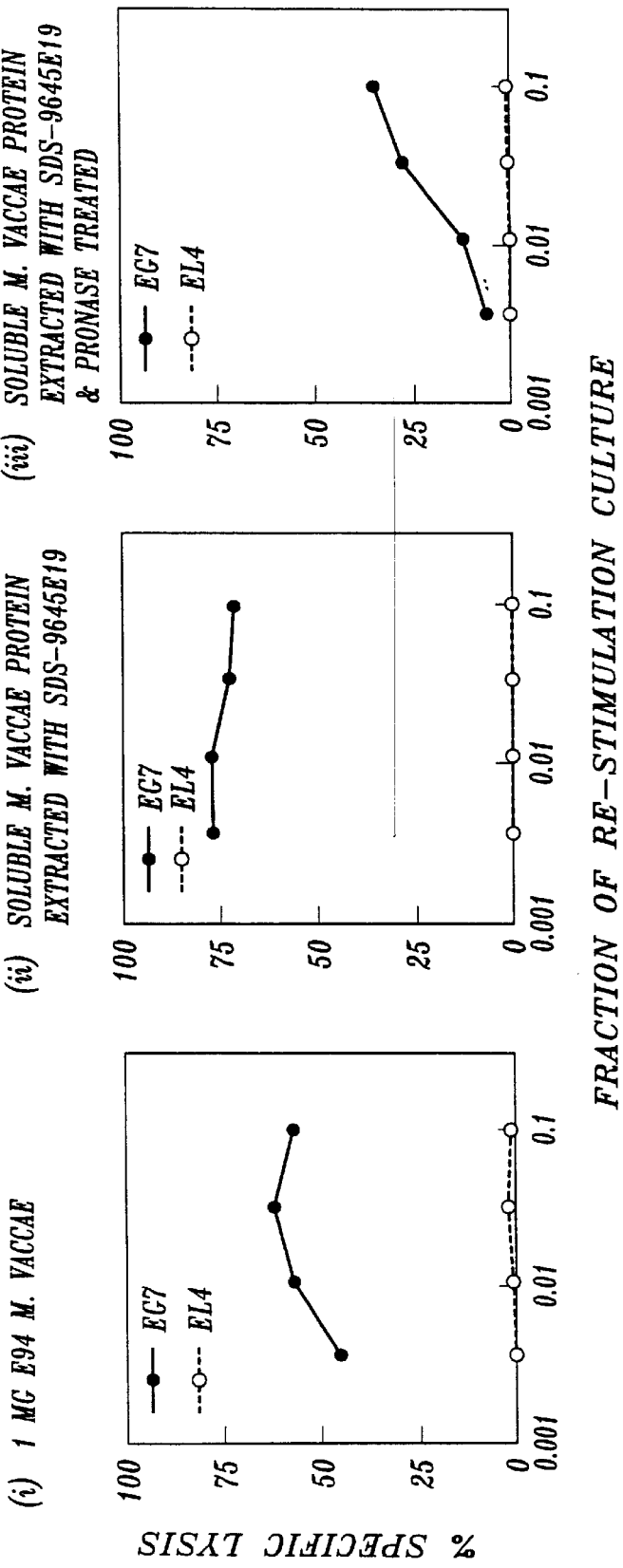
FIG. 4C(i) illustrates the non-specific immune amplifying effects of whole autoclaved M. vaccae.

The diagrams that make up FIG. 4 show the effect of various *M. vaccae* derived adjuvant preparations on the generation of cytotoxic T cells to ovalbumin in C57BL/6 mice. As shown in FIG. 4A, cytotoxic cells were generated in mice immunized with (i) 10 μg, (ii) 100 μg or (iii) 1 mg of autoclaved *M. vaccae* or (iv) 75 μg of *M. vaccae* culture filtrate. FIG. 4B shows that cytotoxic cells were generated in mice immunized with (i) 1 mg whole autoclaved *M. vaccae* or (ii) 1 mg delipidated *M. vaccae*. As shown in FIG. 4C(i), cytotoxic cells were generated in mice immunized with 1 mg whole autoclaved *M. vaccae*; FIG. 4C(ii) shows the active material in 100 μg delipidated *M. vaccae* which then had glycolipids removed and the proteins extracted with SDS. FIG. 4C(iii) shows that active material in the adjuvant preparation of FIG. 4C(ii) was destroyed by treatment with the proteolytic enzyme pronase. By way of comparison, 100 μg of the SDS-extracted proteins had significantly stronger immune-enhancing ability (FIG. 4C(ii)) than did 1 mg whole autoclaved *M. vaccae* (FIG. 4C(i)).

Mice immunized with 1 mg beat-killed *M. vaccae* (FIG. 4D(i)) generated cytotoxic cells to ovalbumin, but mice immunized separately with 1 mg heat-killed *M. tuberculosis* (FIG. 4D(ii)), 1 mg *M. bovis* BCG (FIG. 4D(iii)), 1 mg *M. phlei* (FIG. 4D(iv)), or 1 mg *M. smegmatis* (FIG. 4D(v)) failed to generate cytotoxic cells.

Figure 5:
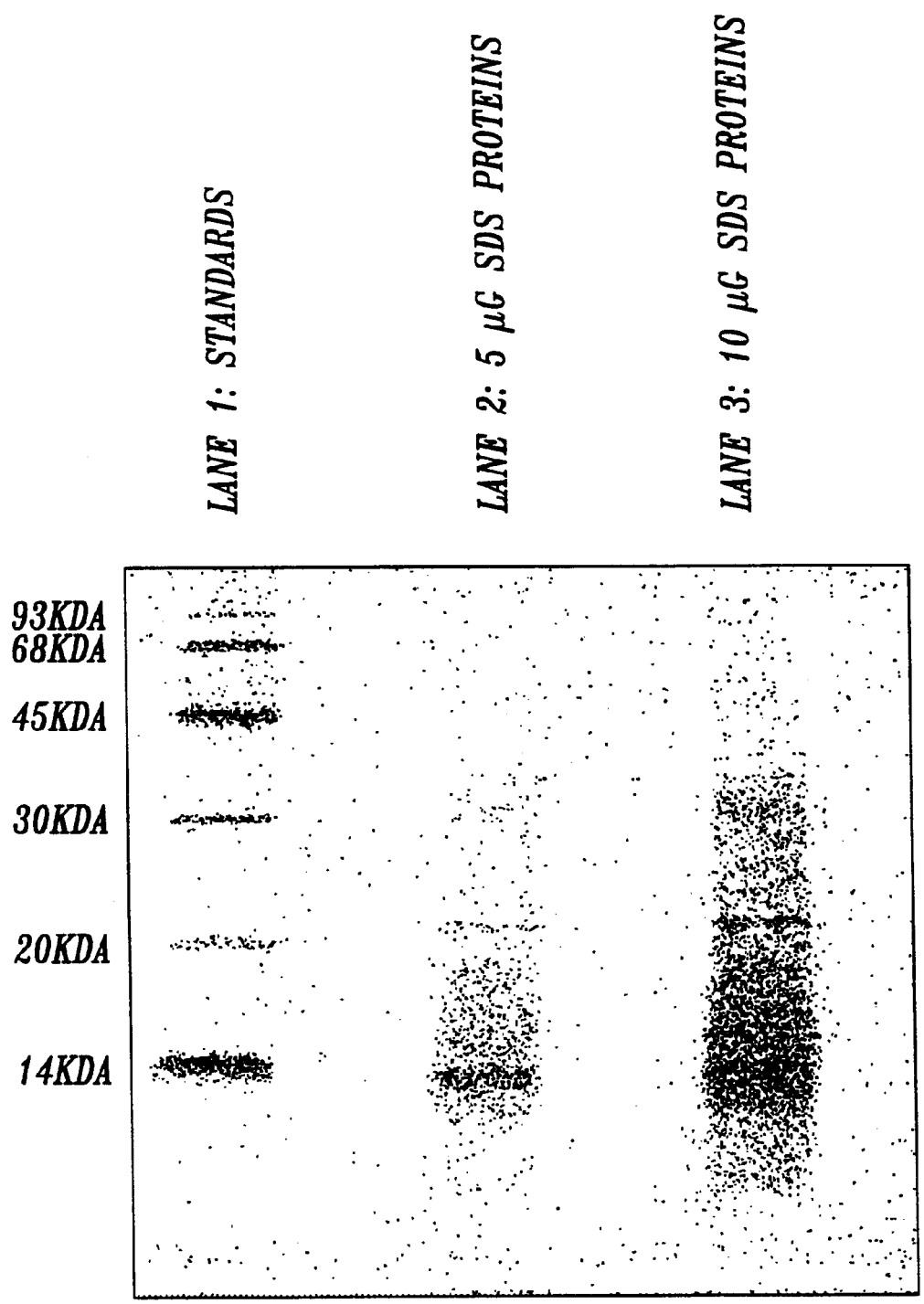
FIG. 5 shows the results of polyacrylamide gel electrophoresis analysis of SDS-extracted proteins derived from delipidated and deglycolipidated M. vaccae.

The SDS-extracted proteins derived from delipidated and deglycolipidated *M. vaccae* were analyzed by polyacrylamide gel electrophoresis. As shown in FIG. 5, three major bands were observed after staining with silver.

EXAMPLE 7

AUTOCLAVED *M. vaccae* GENERATES CYTOTOXIC CD8 T CELLS AGAINST *M. tuberculosis* INFECTED MACROPHAGES This example illustrates the ability of killed *M. vaccae* to stimulate cytotoxic CD8 T cells which preferentially kill macrophages that have been infected with *M. tuberculosis*.

Mice were immunized by the intraperitoneal injection of 500 μg of killed *M. vaccace* which was prepared as described in Example 1. Two weeks after immunization, the spleen cells of immunized mice were passed through a CD8 T cell enrichment column (R&D Systems, St. Paul, Minn., USA). The spleen cells recovered from the column have been shown to be enriched up to 90% CD8 T cells. These T cells, as well as CD8 T cells from spleens of non-immunized mice, were tested for their ability to kill uninfected macrophages or macrophages which have been infected with *M. tuberculosis*.

Macrophages were obtained from the peritoneal cavity of mice five days after they have been given 1 ml of 3% thioglycolate intraperitoneally. The macrophages were infected overnight with *M. tuberculosis* at the ratio of 2 mycobacteria per macrophage. All macrophage preparations were labelled with $^{51}$Chromium at 2 μci per $10^4$ macrophages. The macrophages were then cultured with CD8 T cells overnight (16 hours) at killer to target ratios of 30:1. Specific killing was detected by the release of $^{51}$Chromium and expressed as % specific lysis, calculated as in Example 5.

The production of IFN-γ and its release into medium after 3 days of co-culture of CD8 T cells with macrophages was measured using an enzyme-linked immunosorbent assay (ELISA). ELISA plates were coated with a rat monoclonal antibody directed to mouse IFN-γ (Pharmigen, San Diego, Calif., USA) in PBS for 4 hours at 4 ° C. Wells were blocked with PBS containing 0.2% Tween 20 for 1 hour at room temperature. The plates were then washed four times in PBS containing 0.2% Tween 20, and samples diluted 1:2 in culture medium in the ELISA plates were incubated overnight at room temperature. The plates were again washed, and a biotinylated monoclonal rat anti-mouse IFN-γ antibody (Pharmigen), diluted to 1 μ/ml in PBS, was added to each well. The plates were then incubated for 1 hour at room temperature, washed, and horseradish peroxidase-coupled avidin D (Sigma A-3151) was added at a 1:4,000 dilution in PBS. After a further 1 hour incubation at room temperature, the plates were washed and OPD substrate added. The reaction was stopped after 10 min with 10% (v/v) HCl. The optical density was determined at 490 nm. Fractions that resulted in both replicates giving an OD two-fold greater than the mean OD from cells cultured in medium alone were considered positive.

As shown in Table 2, CD8 T cells from spleens of mice immunized with *M. vaccae* were cytotoxic for macrophages infected with *M. tuberculosis* and did not lyse uninfected macrophages. The CD8 T cells from non-immunized mice did not lyse macrophages. CD8 T cells from naive or non-immunized mice do produce IFN-γ when cocultured with infected macrophages. The amount of IFN-γ produced in coculture was greater with CD8 T cells derived from *M. vaccae* immunized mice.

TABLE 2

EFFECT WITH *M. TUBERCULOSIS* INFECTED MACROPHAGES

| | % Specific Lysis | | IFN-γ (ng/ml) | |
| --- | --- | --- | --- | --- |
| CD8 T cells | uninfected | infected | uninfected | infected |
| Control | 0 | 0 | 0.7 | 24.6 |
| *M. vaccae* Immunized | 0 | 95 | 2.2 | 43.8 |

Although the present invention has been described in some detail by way of illustration and example for purposes of clarity of understanding, changes and modifications can be carried out without departing from the scope of the invention which is intended to be limited only by the scope of the appended claims.

What is claimed is:

1. An isolated polypeptide comprising SEQ ID NO:44.

2. An isolated polypeptide according to claim 1, wherein said polypeptide comprises an amino acid sequence encoded by SEQ ID NO: 41.

3. A composition comprising a polypeptide according to any one of claims 1 and 2, and a physiologically acceptable carrier.

4. A diagnostic kit comprising:

(a) a polypeptide according to any one of claims 1 and 2; and (b) apparatus sufficient to contact said polypeptide with the dermal cells of a patient.

5. A diagnostic kit comprising:

(a) at least one polypeptide according to any one of claims 1 and 2; and (b) a detection reagent.

6. The kit of claim 5 wherein the polypeptide is immobilized on a solid support.

7. The kit of claim 5 wherein the detection reagent comprises a reporter group conjugated to a binding agent.

8. The kit of claim 7 wherein the binding agent is selected from the group consisting of anti-immunoglobulins, Protein G, Protein A and lectins.

9. The kit of claim 7 wherein the reporter group is selected from the group consisting of radioisotopes, fluorescent groups, luminescent groups, enzymes, biotin and dye particles.

10. A fusion protein comprising at least two polypeptides, wherein at least one of the polypeptides comprises SEQ ID NO:44.

11. A composition comprising a polypeptide and a non-specific immune response amplifier, wherein the polypeptide comprises SEQ ID NO:44.

12. A composition according to claim 11 wherein the non-specific immune response amplifier is an adjuvant.

13. A composition according to claim 11 wherein the non-specific immune response amplifier comprises delipidated *M. vaccae* cells.

14. A composition according to claim 11 wherein the non-specific immune response amplifier comprises culture filtrate from *M. vaccae*.

15. A composition comprising a fusion protein according to claim 10 and a physiologically acceptable carrier.

16. A composition comprising a fusion protein according to claim 10 and a non-specific immune response amplifier.

17. A composition according to claim 16, wherein the non-specific immune response amplifier is an adjuvant.

18. A composition according to claim 16 wherein the non-specific immune response amplifier comprises delipidated *M. vaccae* cells.

19. A composition according to claim 16 wherein the non-specific immune response amplifier comprises culture filtrate from *M. vaccae*.

* * * * *